United States Patent
Kishiro et al.

[11] Patent Number: 5,965,824
[45] Date of Patent: Oct. 12, 1999

[54] VIBRATION TYPE MEASURING INSTRUMENT

[75] Inventors: Masami Kishiro; Hironobu Yao, both of Tokyo, Japan

[73] Assignee: Fuji Electric Co., Ltd., Kanagawa, Japan

[21] Appl. No.: 08/925,019

[22] Filed: Sep. 8, 1997

Related U.S. Application Data

[63] Continuation of application No. 08/764,812, Dec. 12, 1996, abandoned.

[30] Foreign Application Priority Data

Dec. 15, 1995 [JP] Japan .................................. 7-326640
Dec. 15, 1995 [JP] Japan .................................. 7-326641

[51] Int. Cl.⁶ .................................................. G01N 9/00
[52] U.S. Cl. .......................... 73/861.357; 73/861.355; 73/861.354; 73/861.351; 73/32 A
[58] Field of Search ................. 73/32 A, 861.351, 73/861.354, 861.355, 861.356, 861.357

[56] References Cited

U.S. PATENT DOCUMENTS

| | | | |
|---|---|---|---|
| 3,080,750 | 3/1963 | Wiley et al. .................... | 73/861.357 |
| 4,680,974 | 7/1987 | Simonsen et al. ............... | 73/861.38 |

(List continued on next page.)

FOREIGN PATENT DOCUMENTS

| | | | |
|---|---|---|---|
| 0698783A1 | 8/1994 | European Pat. Off. .......... | G01F 1/84 |
| 0698783 | 2/1996 | European Pat. Off. .......... | G01F 1/84 |
| 2635866 | 8/1989 | France .......................... | G01F 1/84 |
| 3618798A1 | 12/1987 | Germany ....................... | G01F 21/00 |
| 3808461A1 | 9/1989 | Germany ....................... | G01F 1/84 |
| 3923409 | 1/1991 | Germany ....................... | G01F 1/84 |
| 3923409A1 | 1/1991 | Germany ....................... | G01F 1/84 |
| 4224379 | 12/1993 | Germany ....................... | G01F 1/84 |
| 4224379C1 | 12/1993 | Germany ....................... | G01F 1/84 |
| 4237907A1 | 5/1994 | Germany ....................... | G01F 1/66 |
| 19525253 | 1/1996 | Germany ....................... | G01F 1/84 |
| 19525253A1 | 1/1996 | Germany ....................... | G01F 1/84 |
| 19634663 | 9/1996 | Germany ....................... | G01F 1/84 |

(List continued on next page.)

OTHER PUBLICATIONS

Enoksson P. et al., Fluid Density Sensor based on Resonance Vibration. *Sensors and Actuators A* 46–47, pp. 327–331 (1995).

*Primary Examiner*—Richard Chilcot
*Assistant Examiner*—Jewel V. Thompson
*Attorney, Agent, or Firm*—Elman & Associates

[57] ABSTRACT

A vibration type measuring instrument measures at least one of density and mass flow rate of a fluid in a straight measurement pipe by vibrating the pipe. The vibration type measuring instrument comprises the pipe; a sensor for detecting the vibration of the pipe; and a signal processing circuit for obtaining the resonant angular frequency ω and axial force T based on the detection signal of the sensor, and obtaining the density ρw of the fluid flowing through the pipe using the obtained resonant angular frequency ω and axial force T. The density ρw is obtained by the following equation (E1).

$$\omega^2 = \left\{ EI \int_0^L (d^2y/dx^2)^2 dx - T \int_0^L y(d^2y/dx^2)dx \right\} \bigg/ \left\{ (\rho w Si + \rho t St) \int_0^L y^2 dx + \sum_{k=0}^{n} (mk \cdot yk^2) \right\} \quad (E1)$$

(E: the Young's modulus of the pipe, I: a cross-sectional secondary moment of the pipe, Si: a cross-sectional area of the hollow portion of the pipe, ρt: a density of the pipe, St: the actual cross-sectional area of the pipe, L: the length in the axial direction of the pipe, x: a position in the axial direction of the pipe, y: a vibration amplitude of the pipe at position x, n: a number of masses added to the pipe, mk: a mass of a k-th added mass, and yk: a vibration amplitude of the k-th added mass).

48 Claims, 15 Drawing Sheets

U.S. PATENT DOCUMENTS

| | | | |
|---|---|---|---|
| 4,801,897 | 1/1989 | Flecken | 331/65 |
| 4,803,867 | 2/1989 | Dahlin | 73/861.357 |
| 5,005,400 | 4/1991 | Lew | 73/32 A |
| 5,024,104 | 6/1991 | Dames | 73/861.73 |
| 5,054,326 | 10/1991 | Mattar | 73/861.38 |
| 5,115,683 | 5/1992 | Pratt | 73/861.38 |
| 5,295,084 | 3/1994 | Arunachalam et al. | 364/558 |
| 5,321,991 | 6/1994 | Kalotay | 73/861.37 |
| 5,331,859 | 7/1994 | Zolock | 73/861.356 |
| 5,373,745 | 12/1994 | Cage | 73/861.37 |
| 5,381,697 | 1/1995 | Van Der Pol | 73/861.356 |
| 5,398,554 | 3/1995 | Ogawa et al. | 73/861.38 |
| 5,448,921 | 9/1995 | Cage et al. | 73/861.38 |
| 5,469,748 | 11/1995 | Kalotay | 73/861.38 |
| 5,497,665 | 3/1996 | Cage et al. | 73/861.38 |

FOREIGN PATENT DOCUMENTS

| | | | |
|---|---|---|---|
| 19539049A1 | 4/1997 | Germany | H01L 49/00 |
| 5-69452 | 3/1993 | Japan | B29C 45/14 |
| 569452 | 5/1993 | Japan | G01F 1/84 |
| 6-94501 | 6/1994 | Japan | G01F 1/84 |
| 663958 | 6/1994 | Japan | G01N 9/00 |
| 694501 | 6/1994 | Japan | G01F 1/84 |
| 8706691 | 11/1987 | WIPO | G01F 1/84 |
| 8802477 | 4/1988 | WIPO | G01F 1/84 |
| 8802853 | 4/1988 | WIPO | G01N 9/00 |
| 8900679 | 1/1989 | WIPO | G01F 1/84 |

□ PRIMARY (LINEAR) APPROXIMATION
○ SECONDARY APPROXIMATION (LEAST SQUARES)

| DATA No. | DENSITY [g/cm3] | | | MEASUREMENT PIPE TEMPERATURE [°C] | f1 [Hz] | f3 [Hz] | RATIO fr f3/f1 |
|---|---|---|---|---|---|---|---|
| | TRUE VALUE | COMPUTED VALUE | ERROR | | | | |
| 1 | 0.001 | 0.001 | 0.000 | 22.3 | 836.65 | 4145.5 | 4.9548 |
| 2 | 0.998 | 0.998 | 0.000 | 22.8 | 744.15 | 3687.0 | 4.9546 |
| 3 | 1.887 | 1.886 | -0.001 | 21.5 | 683.45 | 3386.6 | 4.9551 |
| 4 | 0.998 | 0.998 | 0.000 | 24.6 | 754.78 | 3698.5 | 4.9001 |
| 5 | 0.998 | 0.997 | -0.001 | 23.5 | 748.67 | 3692.1 | 4.9315 |
| 6 | 0.998 | 0.998 | 0.000 | 22.4 | 739.80 | 3682.3 | 4.9774 |
| 7 | 0.998 | 0.998 | 0.000 | 21.4 | 733.72 | 3676.0 | 5.0101 |

FIG. 6

| $\rho w$ [g/cc] | $f(\rho w)$ [g/cc] |
|---|---|
| 0.4 | 0.9937 |
| 0.5 | 0.9944 |
| 0.6 | 0.9951 |
| 0.7 | 0.9957 |
| 0.8 | 0.9962 |
| 0.9 | 0.9967 |
| 1.0 | 0.9971 |
| 1.1 | 0.9974 |
| 1.2 | 0.9977 |
| 1.3 | 0.9979 |
| 1.4 | 0.9981 |
| 1.5 | 0.9981 |
| 1.6 | 0.9981 |
| 1.7 | 0.9981 |
| 1.8 | 0.9979 |
| 1.9 | 0.9978 |
| 2.0 | 0.9975 |
| 2.1 | 0.9972 |
| 2.2 | 0.9968 |
| 2.3 | 0.9963 |
| 2.4 | 0.9958 |
| 2.5 | 0.9952 |
| 2.6 | 0.9946 |
| 2.7 | 0.9938 |
| 2.8 | 0.9931 |
| 2.9 | 0.9922 |
| 3.0 | 0.9913 |

FIG. 8

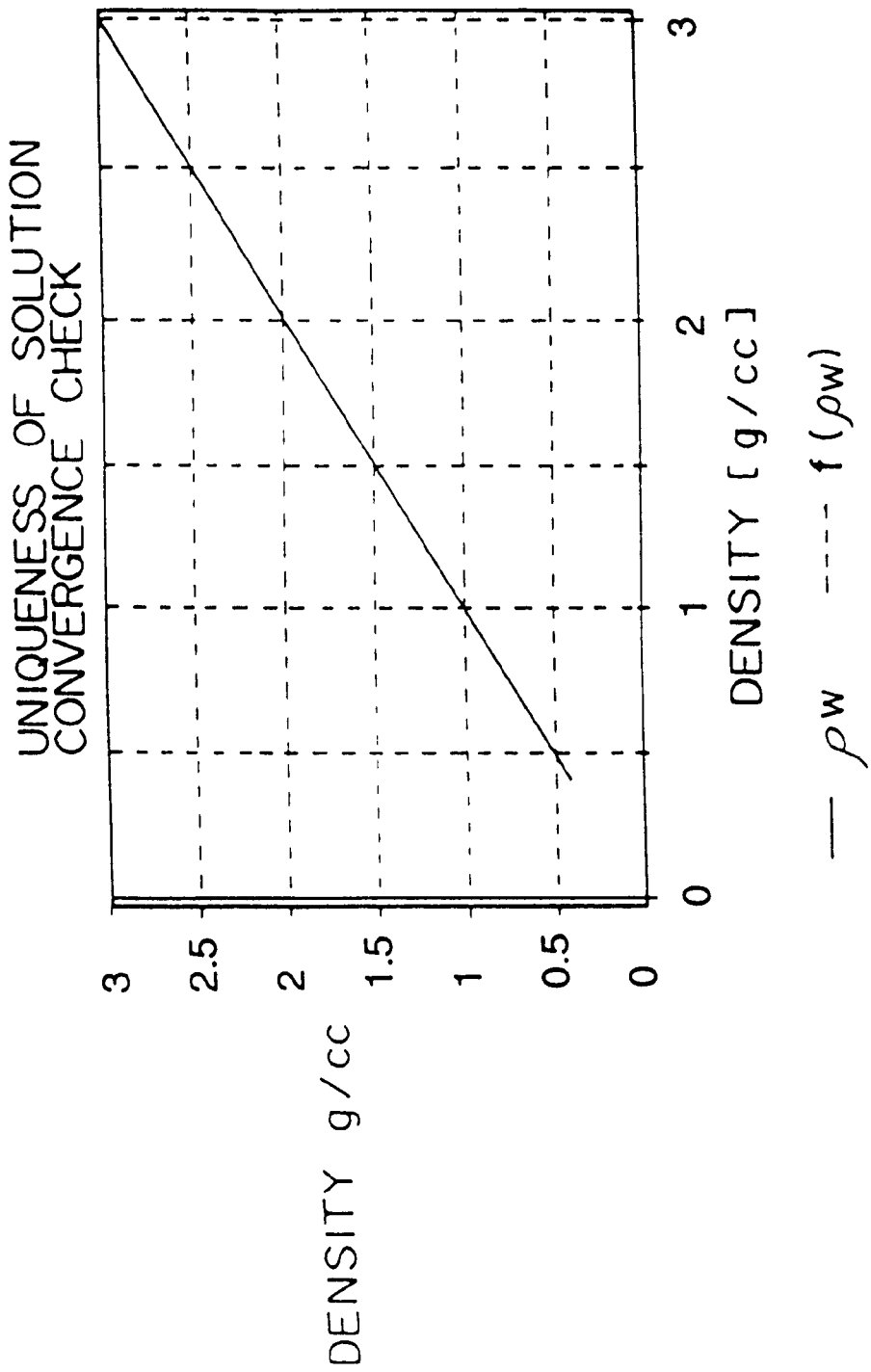
F I G. 9

| $\rho w$ [g/cc] | $f(\rho w)$ [g/cc] |
|---|---|
|  |  |
| 0.400 | 0.994 |
| 0.994 | 0.997 |
| 0.997 | 0.997 |
| 0.997 | 0.997 |
| 0.997 | 0.997 |
|  |  |
| 1.000 | 0.997 |
| 0.997 | 0.997 |
| 0.997 | 0.997 |
| 0.997 | 0.997 |
| 0.997 | 0.997 |
|  |  |
| 2.000 | 0.997 |
| 0.997 | 0.997 |
| 0.997 | 0.997 |
| 0.997 | 0.997 |
| 0.997 | 0.997 |
|  |  |
| 3.000 | 0.991 |
| 0.991 | 0.997 |
| 0.997 | 0.997 |
| 0.997 | 0.997 |
| 0.997 | 0.997 |

FIG. 10

| DATA No. | FLUID DENSITY [g/cc] | | | |
|---|---|---|---|---|
| | ACTUALLY MEASURED VALUE | INITIAL VALUE | COMPUTED VALUE | ERROR |
| 1 | 0.001 | 0.001 | 0.001 | 0.000 |
| | | | | |
| | | 3.000 | -0.007 | -0.008 |
| | | | 0.001 | 0.000 |
| | | | | |
| 2 | 0.997 | 0.997 | 0.998 | 0.000 |
| | | | 0.998 | 0.000 |
| | | | | |
| | | 3.000 | 0.986 | -0.011 |
| | | | 0.998 | 0.000 |
| | | | | |
| 3 | 0.788 | 0.788 | 0.788 | 0.000 |
| | | | 0.788 | 0.000 |
| | | | | |
| | | 3.000 | 0.778 | -0.010 |
| | | | 0.788 | 0.000 |
| | | | | |
| 4 | 1.880 | 1.880 | 1.879 | -0.001 |
| | | | 1.879 | -0.001 |
| | | | | |
| | | 0.400 | 1.885 | 0.005 |
| | | | 1.879 | -0.001 |

FIG. 12

| DATA No. | FLUID DENSITY [g/cc] | | | TEMPERATURE OF PIPE [°C] | MEASURED FREQUENCY VALUE | | | |
|---|---|---|---|---|---|---|---|---|
| | ACTUALLY MEASURED VALUE | COMPUTED VALUE | ERROR | | f1 [Hz] | f3 [Hz] | RATIO fr | CHANGE RATE % |
| 1 | 0.001 | 0.001 | 0.000 | 25.4 | 1025.93 | 5050.3 | 4.9227 | -0.004 |
| 2 | 0.997 | 0.998 | 0.000 | 25.5 | 857.40 | 4220.9 | 4.9229 | 0.000 |
| 3 | 0.788 | 0.788 | 0.000 | 25.8 | 888.02 | 4361.0 | 4.9220 | -0.019 |
| 4 | 1.880 | 1.879 | -0.001 | 25.8 | 763.35 | 3750.2 | 4.9129 | -0.204 |
| 5 | 0.999 | 0.999 | 0.000 | 18.4 | 865.87 | 4235.2 | 4.8913 | -0.643 |
| 6 | 0.999 | 0.999 | 0.000 | 18.2 | 862.95 | 4231.5 | 4.9036 | -0.394 |
| 7 | 0.999 | 0.999 | 0.000 | 17.7 | 860.05 | 4228.2 | 4.9162 | -0.136 |
| 8 | 0.999 | 0.999 | 0.000 | 16.4 | 856.18 | 4224.1 | 4.9337 | 0.220 |
| 9 | 0.999 | 0.999 | 0.000 | 16.0 | 853.32 | 4220.8 | 4.9463 | 0.475 |

FIG. 13

| DATA No. | FLUID DENSITY [ g / cc ] | | |
|---|---|---|---|
| | ACTUALLY MEASURED VALUE | COMPUTED VALUE | ERROR |
| | | | |
| 1 | 0.001 | 0.001 | 0.000 |
| 2 | 0.997 | 0.998 | 0.000 |
| 3 | 0.788 | 0.788 | 0.000 |
| 4 | 1.880 | 1.884 | 0.004 |
| | | | |
| 5 | 0.999 | 0.999 | 0.000 |
| 6 | 0.999 | 0.999 | 0.000 |
| 7 | 0.999 | 0.999 | 0.000 |
| 8 | 0.999 | 0.999 | 0.000 |
| 9 | 0.999 | 0.999 | 0.000 |

FIG. 14

VIBRATION TYPE MEASURING INSTRUMENT

This application is a continuation of application Ser. No. 08/764,812 filed Dec. 12, 1996, now abandoned.

BACKGROUND OF THE INVENTION

1. Field of the Invention

The present invention relates to a vibration type measuring instrument for measuring at least one of density and mass flow rate of a fluid flowed in a straight measurement pipe by vibrating the straight measurement pipe.

2. Description of the Related Art

FIG. 1A shows the configuration of an example of a vibration type measurement instrument. FIG. 1B is a top view of the detecting unit of the vibration type measuring instrument.

The vibration type measuring instrument comprises a detecting unit 1, a driving circuit 8, and a signal processing circuit 9 as shown in FIG. 1A. The detecting unit 1 comprises a hollow straight measurement pipe 2, fixtures 3a and 3b for fixing both ends of the straight measurement pipe 2, supporters 4a and 4b for connecting the fixtures 3a and 3b, a driver 5 for vibrating the straight measurement pipe 2, sensors 6a and 6b for detecting the vibration of the straight measurement pipe 2, and adapters 7a, 7b, and 7c for respectively fixing the driver 5 sensors 6a and 6b as shown in FIGS. 1A and 1B. The straight measurement pipe 2 is provided with a temperature sensor 10 for detecting the temperature of the measurement pipe.

The straight measurement pipe 2 is connected to external pipes not shown in FIG. 1A in such a way that the fluid to be measured can flow through the straight measurement pipe 2. Both ends of the straight measurement pipe 2 are fixed with wax or welded to the fixtures 3a and 3b respectively so that the end portions can be vibration nodes. The supporters 4a and 4b stably support the driver 5, and sensors 6a and 6b. They have greater rigidity than the straight measurement pipe 2, and are connected to the fixtures 3a and 3b through soldering, welding, etc. The sensors 6a and 6b can be speed detecting sensors, displacement sensors, acceleration sensors, etc.

The driver 5 is mounted at the center of the straight measurement pipe 2. The sensors 6a and 6b are mounted symmetrically about the driver 5 in contact with the measurement pipe. When the vibration type measuring instrument is used as a Coriolis mass flow meter, the density of the fluid is measured using at least one of the sensors 6a and 6b by the method described below. Simultaneously, the mass flow rate of the fluid is measured based on the phase difference (time difference) of the fluid vibration between the two sensors 6a and 6b mounted up stream and down stream of the driver 5. When the vibration type measuring instrument is used as a density meter for only measuring the density of a fluid, only one of the sensors 6a and 6b may be mounted (for example, the sensor 6a only) as a sensor for measuring the density.

The straight measurement pipe 2 is vibrated at its resonant frequency by the driver 5 operated according to the drive signal from the driving circuit 8. The detection signals from the sensors 6a and 6b and the temperature detection signal from the temperature sensor 10 are transmitted to the signal processing circuit 9. The signal processing circuit 9 obtains the resonant frequency of the straight measurement pipe 2 according to the detection signals from the sensors 6a and 6b, and calculates the density of the fluid by the operation described below, according to the resultant resonant frequency and the temperature of the straight measurement pipe 2.

The following differential equation (1) is expressed relating to the straight measurement pipe 2 having uniform cross-section, where E indicates the Young's modulus of the straight measurement pipe 2; I indicates the cross-sectional secondary moment of the straight measurement pipe 2; x indicates a position on the straight measurement pipe 2 in the axial direction (x=0 at one end of the measurement pipe 2, and x=L at the other end of the measurement pipe 2); y indicates the vibration amplitude of the straight measurement pipe 2 at the position x (a function with the variable x); ρw indicates the density of the fluid; Si indicates the cross-sectional area of the hollow portion of the straight measurement pipe 2; ρt indicates the density of the straight measurement pipe 2; St indicates the cross-sectional area of the straight measurement pipe 2; and t indicates time.

$$EI(\partial^4 y/\partial x^4)+(\rho wSi+\rho tSt)(\partial^2 y/\partial t^2)=0 \quad (1)$$

Solving the equation (1) using given boundary conditions, the resonant frequency f of the horizontal vibration of the straight measurement pipe 2 is obtained by the following equation (2).

$$f=\lambda^2\{EI/(\rho wSi+\rho tSt)\}^{1/2}/(2\pi L^2) \quad (2)$$

(λ indicates the constant determined by the boundary conditions and vibration mode of the straight measurement pipe 2; and L indicates the length of the straight measurement pipe 2 in the axial direction)

The above described equation (2) is solved for ρw as indicated below.

$$\rho w\{(\lambda^4 EI/4\pi^2 L^4 f^2)-\rho tSt\}/Si \quad (3)$$

The density ρw of the fluid can be obtained by substituting the detected resonant frequency f of the straight measurement pipe 2 in the above equation (3), and further substituting the Young's modulus E after a temperature amendment is performed based on the temperature of the straight measurement pipe 2 measured by the temperature sensor 10, the secondary cross-sectional moment I obtained by amending the thermal expansion according to the temperature, length L of the measurement pipe, and the cross-sectional areas St and Si.

However, in the case of the device using the straight measurement pipe 2 as shown in FIG. 1, a temperature difference arises between the straight measurement pipe 2 and the supporters 4a and 4b by a change in temperature of, for example, the fluid, surrounding atmosphere, etc., thereby generating a force (axial force) in the straight measurement pipe 2 in the axial direction. The axial force changes, as is well-known, the resonant frequency f of the straight measurement pipe 2, and generates an error in the density ρw calculated by the above described equation (3).

The conventional countermeasures to the above problems are to prevent the influence of the axial force by providing a curved measurement pipe, applying a bellows or diaphragm structure at both ends of the measurement pipe, etc., or to limit the difference in temperature between the fluid and the surrounding atmosphere. However, a curved measurement pipe raises hygienic problems such as corrosions caused by the puddles of the fluid, which is hard to clean, and can create a large pressure loss in the fluid, thereby making problems for the user. There are additional problems with the bellows and diaphragm structures in that they are complicated in configuration, they are weak against shock when transported because of their mechanical fragility, and they cannot completely eliminate the axial force. Additionally, the method of limiting the temperature difference between the fluid and the surrounding atmosphere imposes large limitations on field online measurements. This is not a desired phenomenon in measurement technology.

Another method of solving the problem due to axial force changes, is to amend a measured density value based on the measured axial force by measuring the axial force working on the measurement pipe by measuring the temperature difference between the measurement pipe and a supporter, measuring the distortion of the measurement pipe using a strain gauge, etc. However, this method also has the following problems.

That is, the above described differential equation (1) is expressed as follows when the axial force (tension) T is present.

$$EI(\partial^4 y/\partial x^4) - T(\partial^2 y/\partial x^2) + (\rho wSi + \rho tSt)(\partial^2 y/\partial t^2) = 0 \quad (4)$$

Solving the differential equation (4) under the given boundary conditions, the equations (2) and (3) for obtaining the density values, which are expressed as follows, are obtained.

$$g(f, \rho w, T, E, I, Si, \rho t, St) = 0 \quad (5)$$

This is an extremely complicated function not explicitly containing the density $\rho w$. Therefore, in this case, the density $\rho w$ cannot be directly obtained as shown by equation (3), and a numerical analysis such as a successive approximation cannot be applied in practical use because of the complicated equation.

In addition to the above described problems, the mass of the components in contact with or added to the measurement pipe, such as the driver 5, sensors 6a and 6b, and temperature sensor 10, can be a factor in lowering the density measurement precision. The inertial force of such an added mass functions as a shearing force for the measurement pipe, and furthermore complicates the differential equation (4) and function (5), thereby making the computation of the density $\rho w$ more difficult.

In the method of obtaining the axial force based on the temperature difference between a measurement pipe and a supporter, the temperature distribution of the supporter changes with the thermal conductivity of the supporter and the temperature of the fluid and the surrounding atmosphere, therefore the axial force cannot be correctly measured. The method of fixing a strain gauge to a measurement pipe has problems in the fixing technology and long-term reliability. Therefore, it is difficult to use this method for mass production.

SUMMARY OF THE INVENTION

The present invention aims at improving the measurement precision of a vibration type measuring instrument by obtaining the density and the mass flow rate of a fluid by an appropriate method using a straight measurement pipe, suitable for mass production and accurate measurement. The present invention further aims at improving the measurement precision of a vibration type measuring instrument by obtaining an axial force applied to the measurement pipe with high precision and amending the influence of the axial force on the measurement of the density and the mass flow rate of the fluid.

The vibration type measuring instrument according to the present invention measures at least one of the mass flow rate and the density of the fluid flowing through a straight measurement pipe by vibrating the pipe. The vibration type measuring instrument includes a straight measurement pipe; a vibration detecting unit for detecting a vibration of the measurement pipe; and a signal processing unit for obtaining the resonant angular frequency $\omega$ and axial force T of the measurement pipe based on the detection signal of the vibration detecting unit, and obtaining the density $\rho w$ of the fluid flowing through the measurement pipe based on the following equation (E1) using the obtained resonant angular frequency $\omega$ and axial force T.

$$\omega^2 = \left\{ EI \int_0^L (d^2 y/dx^2)^2 dx - T \int_0^L y(d^2 y/dx^2) dx \right\} / \left\{ (\rho wSi + \rho tSt) \int_0^L y^2 dx + \sum_{k=0}^n (mk \cdot yk^2) \right\} \quad (E1)$$

where E indicates the Young's modulus of the measurement pipe, I indicates the cross-sectional secondary moment of the measurement pipe, Si indicates the cross-sectional area of the hollow portion of the measurement pipe, $\rho t$ indicates the density of the measurement pipe, St indicates the actual cross-sectional area of the measurement pipe, L indicates the length in the axial direction of the measurement pipe, x indicates a position in the axial direction of the measurement pipe, y indicates the vibration amplitude of the measurement pipe at position x, n indicates the number of masses added to the measurement pipe, mk indicates the mass of the k-th added mass, and yk indicates the vibration amplitude of the k-th added mass.

The signal processing unit calculates the density $\rho w$ of the fluid flowing through the measurement pipe by the following equation (E2) which is obtained by solving the above described equation (E1) for the density $\rho w$ using the constants A, B, and C determined by the vibration form or mode of the measurement pipe and the added mass.

$$\rho w = (AEI/\omega^2 L^4 Si) + (BT/\omega^2 L^2 Si) + (C/LSi) \quad (E2)$$

The above described constants A, B, and C can be determined by solving the simultaneous equations including three different equations obtained by substituting in the above described equation (E2) three sets of values of the density $\rho w$ of the fluid, the Young's modulus E, the cross-sectional secondary moment I, the resonant angular frequency $\omega$, the axial force T, the length L, and the cross-sectional area Si, which are obtained in three different states.

The above described constants A, B, and C can be determined using the least squares method in a way that the error among at least three equations can be minimized after generating at least three different equations by substituting in the above described equation (E2) three sets of values, obtained in at least three different states, of the density $\rho w$ of the fluid, the Young's modulus E, the cross-sectional secondary moment I, the resonant angular frequency $\omega$ and the axial force T, the length L, and the cross-sectional area Si.

The above described signal processing unit can obtain the axial force T based on the ratio of the resonant frequency between the first vibration mode of the measurement pipe and the resonant frequency of the second vibration mode. The above described first and second vibration modes may be respectively the primary and tertiary vibration modes of the measurement pipe. The above described first and second vibration modes may be respectively the tertiary and quinary vibration modes of the measurement pipe. The above described axial force T can be obtained by the following equation (E3) using an integer u equal to or larger than 0 and a coefficient $a_j$ indicating the relationship between the resonant frequency ratio fr of the two vibration modes of the measurement pipe and the axial force T.

$$T = \sum_{j=0}^{\mu} (a_j \cdot fr^j) \quad (E3)$$

The integer u can be, for example, 2.

The above described signal processing unit can obtain the density ρw of the fluid flowing through the measurement pipe as a convergence value of a sequence $\{\rho w_n\}$ with the initial value $\rho w_c$ given, where the $\rho w_n$ of the sequence $\{\rho w_n\}$ can be represented by the following equation (E4) using the constants A, B, and C determined by the vibration form of the measurement pipe and the mass added.

$$\rho w_n = (AEI/\omega^2 L^4 Si) + (BT(fr, \rho w_{n-1})/\omega^2 L^2 Si) + (C/LSi) \quad (E4)$$

The density of the fluid measured as described above is applied to the above described initial value $\rho w_0$ in the next measurement. The value $\rho w_v$ obtained by operating the sequence $\{\rho w_v\}$ v (an integer equal to or larger than 1) times can be applied to the density ρw. The value v can be, for example, 1.

The signal processing unit can obtain the above described axial force T based on the ratio fr of the resonant frequency of the first vibration mode in the measurement pipe and the resonant frequency in the second vibration mode of the measurement pipe.

The signal processing unit can obtain the axial force T(fr, ρw) as a function Tr expressed by the following equation (E5) using the ratio fr of the resonant frequencies and the function fd (ρw) indicating the influence of the density ρw of the fluid.

$$T(fr, \rho w) = Tr\{fr/fd(\rho w)\} \quad (E5)$$

The above described axial force T(fr, ρw) can also be obtained by the following equation (E6) using an integer p equal to or larger than 0 and the coefficient indicating the relationship between $\{fr/fd(\rho w)\}^j$ and the function Tr. The integer p can be, for example, 2.

$$Tr\{fr/fd(\rho w)\} = \sum_{j=0}^{p} [bj\{fr/fd(\rho w)\}^j] \quad (E6)$$

The function fd(ρw) can also be obtained by the following equation (E7) using an integer u equal to or larger than 0 and a coefficient aj indicating the relationship between the density ρw of the fluid and the function fd.

$$fd(\rho w) = \sum_{j=0}^{\mu} (aj \cdot \rho w^j) \quad (E7)$$

where the integer u can be either 2 or 3.

The method according to the present invention is to measure at least one of the mass flow rate and the density of the fluid flowing through a straight measurement pipe by vibrating the pipe. This method includes the steps of detecting the vibration of the measurement pipe, obtaining the resonant angular frequency ω and axial force T of the measurement pipe based on the detected vibration of the measurement pipe, and obtaining the density ρw of the fluid flowing through the measurement pipe by the above described equation (E1) using the obtained resonant angular frequency ω and axial force T.

This method can also include the step of obtaining the density ρw of the fluid flowing through the measurement pipe by the above described equation (E2) using the constants A, B, and C determined by the vibration form of the measurement pipe and the added mass.

This method can include the step of obtaining three different equations by substituting in the above described equation (E2) three sets of values, obtained in three different states, of the density ρw of the fluid, the Young's modulus E of the measurement pipe, the cross-sectional secondary moment I of the measurement pipe, the resonant angular frequency ω and axial force T of the measurement pipe, the length L of the measurement pipe in the axial direction, the cross-sectional area Si of the hollow portion of the measurement pipe, and the step of determining the constants A, B, and C by solving the simultaneous equations of the three different equations.

This method can include the step of obtaining at least three different equations by substituting in the above described equation (E2) three sets of values, obtained in at least three different states, of the density ρw of the fluid, the Young's modulus E, the cross-sectional secondary moment I, the resonant angular frequency ω and axial force T, the length L, and the cross-sectional area Si, and the step of determining the constants A, B, and C by a least squares method in a way that the error among at least three equations can be minimized.

This method can include the step of obtaining the axial force T based on the ratio of the resonant frequency of the first vibration mode of the measurement pipe to the resonant frequency of the second vibration mode. The above described first and second vibration modes can also be respectively the primary and tertiary vibration modes of the measurement pipe. The above described first and second vibration modes can also be respectively the tertiary and quinary vibration modes of the measurement pipe.

This method can also include the step of obtaining the axial force T by the above described equation (E3) using an integer u equal to or larger than 0 and a coefficient $a_j$ indicating the relationship between the resonant frequency ratio fr of the two vibration modes of the measurement pipe and the axial force T. The integer u can be, for example, 2.

This method can include the step of obtaining the density ρw of the fluid flowing through the measurement pipe as a convergence value of the sequence $\{\rho w_n\}$ with the initial value $\rho w_0$ given. It may also include the step of applying the density ρw of the measured fluid to the initial value $\rho w_0$.

This method can include the step of applying the value $\rho w_v$ obtained by operating the sequence $\{\rho w_n\}$ v (an integer equal to or larger than 1) times to the density ρw. The value v can be, for example, 1.

This method can also include the step of obtaining the above described axial force T based on the ratio fr of the resonant frequency of the first vibration mode of the measurement pipe to the resonant frequency of the second vibration mode of the measurement pipe. This method can further include the step of obtaining the axial force T (fr,ρw) as the function Tr appearing in the above described equation (E5).

This method can further include the step of obtaining the function Tr by the equation (E6). In this case, the integer p can be, for example, 2. The method further includes the step of obtaining the function fd by the above described equation (E7). In this case, the integer u can be either 2 or 3.

BRIEF DESCRIPTION OF THE DRAWINGS

FIG. 6 is a table showing the correspondence between the density of a fluid measured by the vibration type measuring instrument according to the present invention and its true value;

FIG. 8 is a table showing the density ρw and f(ρw) of the fluid obtained by the vibration type measuring instrument according to the second embodiment;

FIG. 9 is a graph showing the relationship between the density ρw and f (ρw) of the fluid obtained by the vibration type measuring instrument according to the second embodiment;

FIG. 10 is a table showing the result of checking the speed of the convergence of the function fd (ρw);

FIG. 12 is a table showing the convergence using the iterative method;

FIG. 13 is a table showing the fluid density measured according to the present invention, the temperature of the measurement pipe, and the resonant frequency of the measurement pipe;

FIG. 14 is a table showing the result of different density computations on a measured value shown in the table of FIG. 13.

DESCRIPTION OF THE PREFERRED EMBODIMENT

Figure 1A:
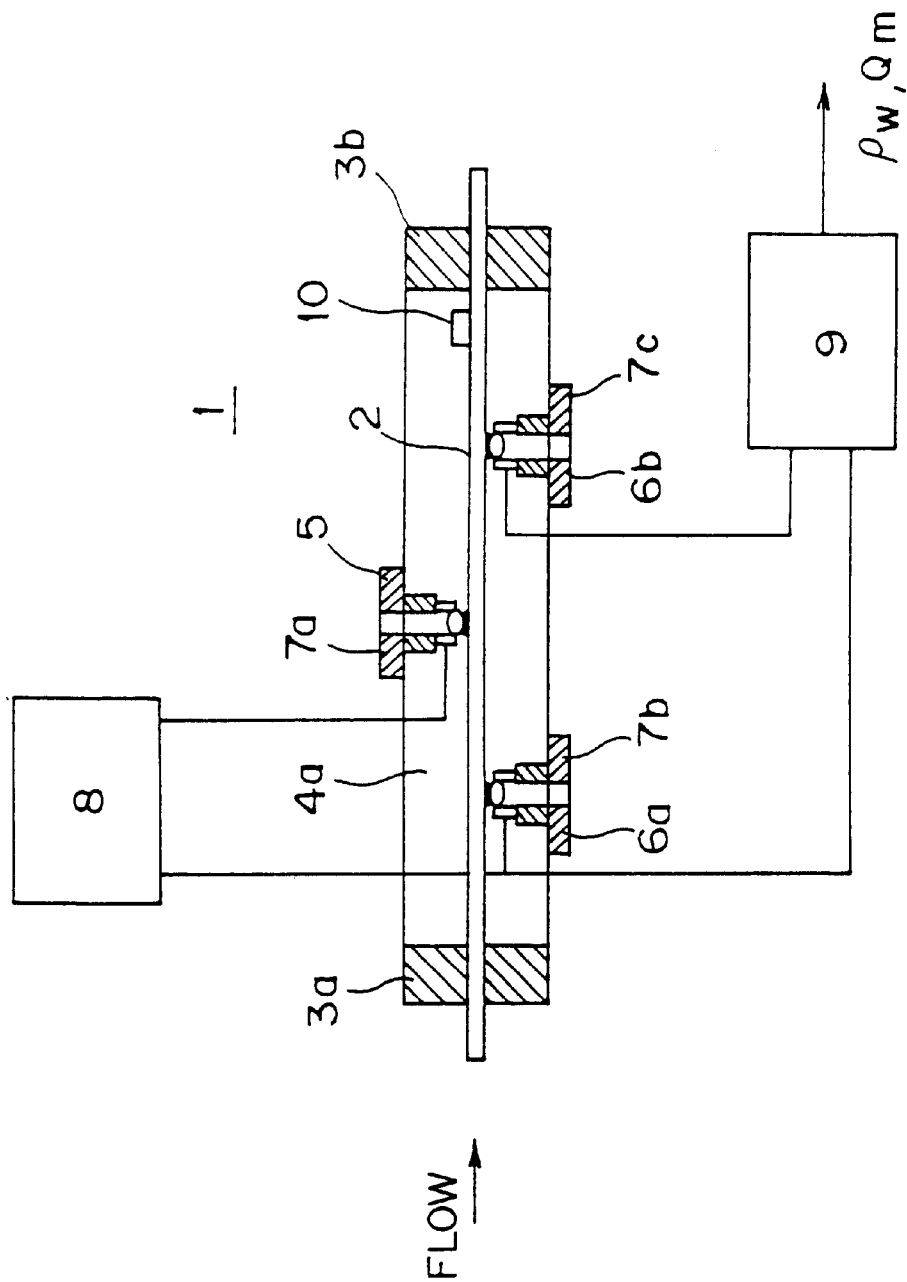
FIG. 1A shows the configuration of an example of a vibration type measuring instrument.
Figure 1B:
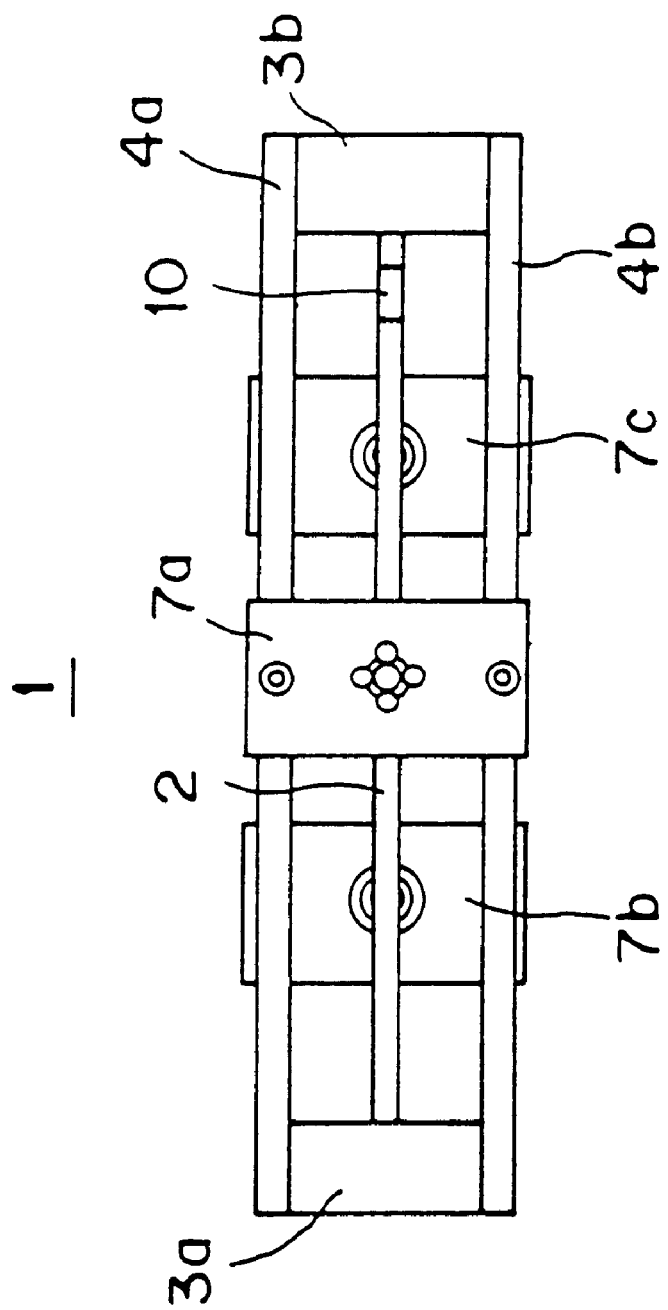
FIG. 1B is a top view of the example of the vibration type measuring instrument.
Figure 2:
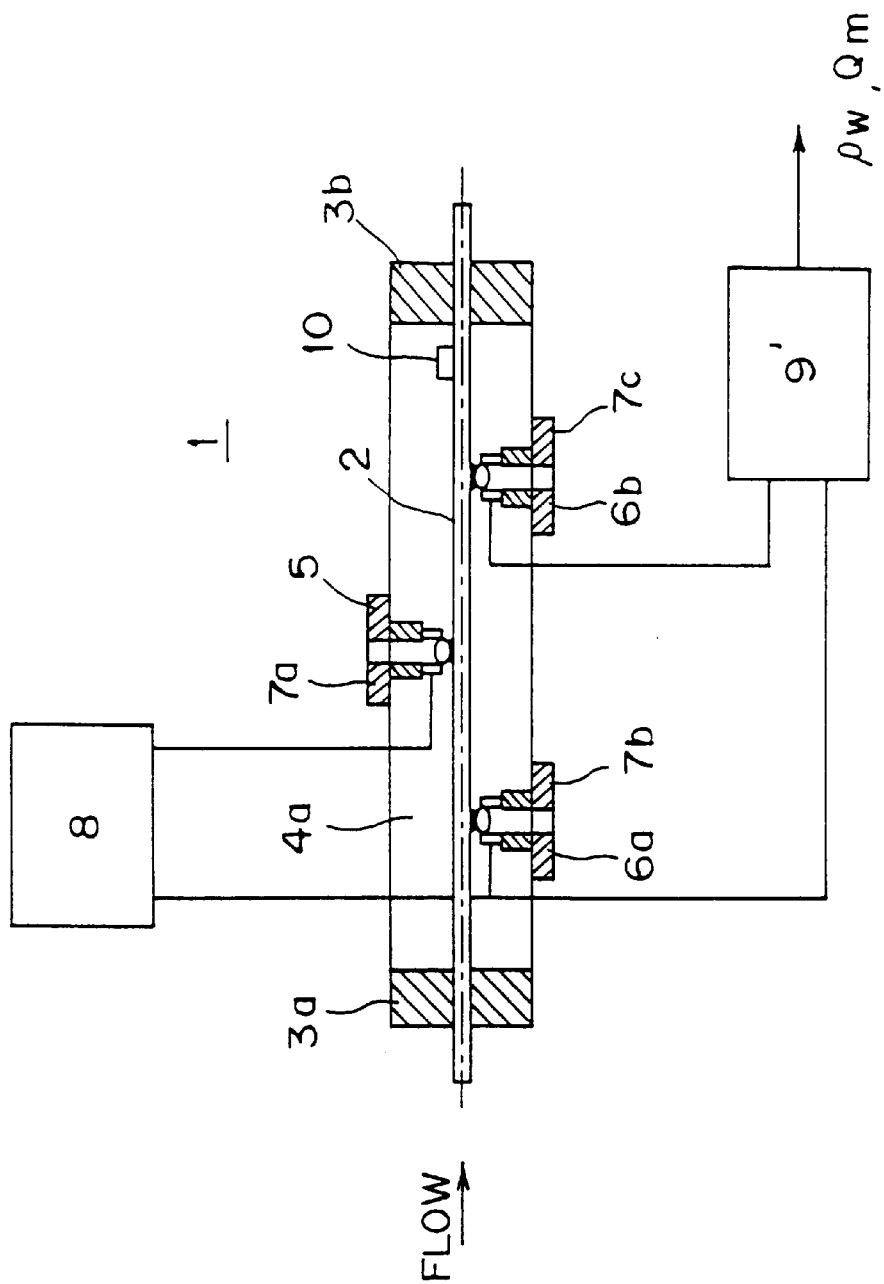
FIG. 2 shows the configuration of the first embodiment of the vibration type measuring instrument according to the present invention.

FIG. 2 shows the first embodiment of the vibration type measuring instrument according to the present invention. Of the components of the first embodiment, those with the same function as shown in FIGS. 1A and 1B are given the same reference numbers, and the description is omitted here.

As shown in FIG. 2, the vibration type measuring instrument according to the first embodiment includes the detecting unit 1, the driving circuit 8, and a signal processing circuit 9'. The detecting unit 1 and driving circuit 8 are the same as those shown in FIGS. 1A and 1B. The signal processing circuit 9' obtains the resonant frequency of the straight measurement pipe 2 according to the signals from the sensors 6a and 6b, and computes the fluid density ρw and mass flow rate Qm according to the obtained resonant frequency.

When an axial force (tension) T effects the straight measurement pipe 2, the differential equation used in computing the density is the above described equation (4). Even if the equation is solved under given boundary conditions, the equation expressing the density refers to an extremely complicated function which does not explicitly include the density ρw, as indicated in the above described equation (5). Therefore, according to the present embodiment, the Rayleigh method for determining a resonant angular frequency ω is applied to the vibration type measuring instrument provided with a straight measurement pipe. The signal processing circuit 9' according to the present embodiment computes the density ρw by the Rayleigh method and corrects the measurement error caused by the axial force and added mass.

It is confirmed by the Inventors of the present invention that the equation based on the Rayleigh method according to the present invention is expressed by the following equation (6).

$$\omega^2 = \left\{ EI \int_0^L (d^2y/dx^2)^2 dx - T \int_0^L \frac{y(d^2y/dx^2)dx}{\left\{(\rho wSi + \rho tSt)\int_0^L y^2 dx + \sum_{k=1}^n (mk \cdot yk^2)\right\}} \right. \tag{6}$$

where mk indicates the mass value of the k-th (k=1–n) added mass, and yk indicates the vibration amplitude of the k-th added mass.

The equation (6) features a number of advantages as follows:

(a) The influence of the axial force and added mass can be corrected.

(b) Since the equation is simple, it can be easily and explicitly solved for the density ρw.

(c) Practically acceptable density measurement precision can be obtained.

Therefore, according to the present embodiment, precise density measurement is realized using a simply-designed and easily-operated straight measurement pipe.

Although the equation (6) contains a plurality of integral terms, it is not actually required according to the Inventor that these integral terms are processed in each operation. The integral terms can be replaced with predetermined constants. The following equation (7) is a variation of equation (6), and is explicitly solved for the density ρw. The constants A, B, and C in equation (7) replace the integral terms and summation term Σ in equation (6).

$$\rho w = (AEI/\omega^2 L^4 Si) + (BT/\omega^2 L^2 Si) + (C/LSi) \tag{7}$$

Using the constants A, B, and C, the equation is expressed in a simple form and the density can be easily computed. The constants A, B, and C can be predetermined based on experiments, etc. to obtain a sufficiently precise density value.

It is not practical that the constants A, B, and C in equation (7) are obtained by integration. A dimensional error and residual stress from assembly may remain in the detecting unit 1 of the vibration type measuring instrument shown in FIG. 2. Therefore, to improve the density measurement precision, it is desired to actually measure the density and amend the constants A, B, and C. The amendments are made as follows.

The values of $\rho w$, E, I, $\omega$, L, Si, and T are measured in a given state. An equation having three unknown numbers A, B, and C is generated by substituting these values in equation (7). The values are obtained three times in different states (with density, temperature, axial force, etc. altered) to generate three equations. Solving these equations as simultaneous equation can obtain the three unique unknown numbers. Since the constants A, B, and C are determined according to the actually measured values in this method, more appropriate constants can be obtained for the measuring instrument, thereby improving the measurement precision. However, unless each equation of the simultaneous equations is independent of the others, the constants A, B, and C cannot be uniquely determined. If they indicate a small degree of independence, then obtained constants A, B, and C may generate a large error. Therefore, it is desired that each equation is processed in three completely independent states.

The following method can also be used in determining the constants.

That is, the measurements are taken in altered states more than three times. Thus, the number of equations becomes larger than the number of unknown numbers. As a result, there are no set of constants A, B, and C that satisfy all equations. Therefore, the constants A, B, and C are determined in such a way that the error can be minimized by the least squares method. Although there is more effort required to take measurements in this method, the measured values in a larger number of states can be reflected on the determination of the constants A, B, and C. Therefore, it is effective when a high average measurement precision is required over a larger range of use corresponding to a number of states.

When equations (6) and (7) are used, an axial force working on the measurement pipe should be obtained to compute the density $\rho w$. The above described equation (2) is used to obtain the resonant frequency f of the measurement pipe without consideration of the axial force T. In consideration of the axial force T, equation (2) is converted into equation (8).

$$fv = \lambda v(T)^2 \{EI/(\rho wSi - \rho tSt)\}^{1/2}/(2\pi L^2) \qquad (8)$$

where fv indicates the resonant frequency of the v-th mode of the measurement pipe, and $\lambda v$ indicates the v-th mode constant of the measurement pipe (a function of T).

The ratio fr of the resonant frequency fv and the resonant frequency fq in two optional vibration modes, that is, the v-th and q-th modes respectively of the straight measurement pipe 2, is computed by the following equation (9) obtained from the above described equation (8).

$$fr = \lambda v(T)^2 / \lambda q(T)^2 \qquad (9)$$

The equation refers to a function with an axial force only. Therefore, computing the ratio between the resonant frequencies of the two modes of the straight measurement pipe 2 allows calculation of the axial force T.

Since two resonant frequencies are measured in this method, the straight measurement pipe 2 of the detecting unit 1, the sensors 6a and 6b for detecting the vibration of the straight measurement pipe 2, and the existing vibration system using the driver 5 can be used as they are, although the design of the driving circuit 8 and the signal processing circuit 9' shown in FIG. 2 becomes a little complicated. Therefore, it is not necessary to design a complicated structure for the detecting unit 1. Furthermore, since the axial force can be directly measured, this method obtains a higher-precision measurement than the method of obtaining the axial force based on the temperature difference between the measurement pipe 2 and the supporters 4a and 4b. Furthermore, this method is more suitable for mass production and attains a higher reliability than the method of fixing the strain gauge to the measurement pipe.

Figure 3A:
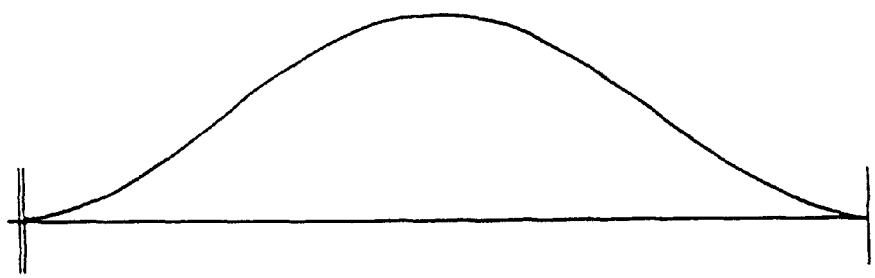
FIG. 3 shows the vibration state of the measurement pipe in three vibration modes.
Figure 3B:
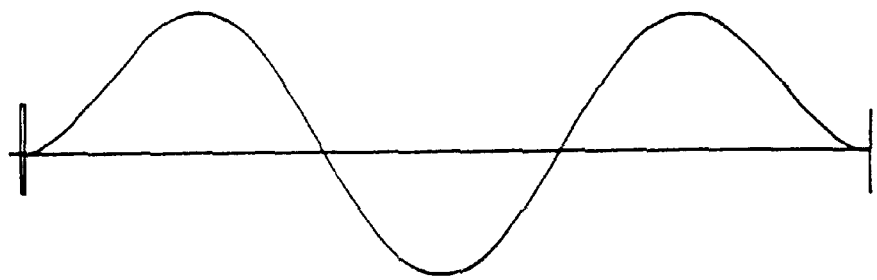
Figure 3C:
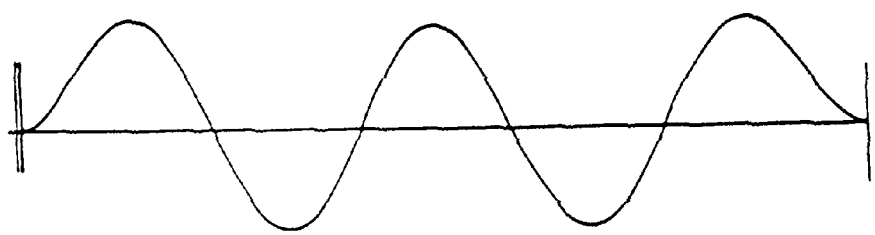

FIG. 3 shows the vibration states of the measurement pipe 2 in three vibration modes. (a) in FIG. 3 indicates the vibration in the primary mode, (b) indicates the vibration in the tertiary mode, and (c) indicates the vibration in the quinary mode.

Normally, the measurement pipe 2 shown in FIG. 2 has a great number of vibration modes. The axial force can be computed by equation (9) using the ratio between the resonant frequencies of any two of the vibration modes. However, when the resonant frequency is actually measured, the measurement pipe is made to resonate and the resultant frequency is measured, or the frequency is swept to measure the transmission function, and so forth. In any method, it is desired that an odd-ordinal-number mode, in which the central portion of the measurement pipe indicates an antinode of the vibration, is selected when the driver 5 is provided at the center of the straight measurement pipe 2 as in the detecting unit 1 shown in FIG. 2. Normally, excitation and measurement are easily made in a smaller-ordinal-number mode at a lower frequency. According to the study of the Inventors, it is apparently convenient to use the ratio between the resonant frequency in the primary (1st) mode and the resonant frequency in the tertiary (3rd) mode, or the ratio between the resonant frequency in the tertiary (3rd) mode and the resonant frequency in the quinary (5th) mode.

Figure 4:
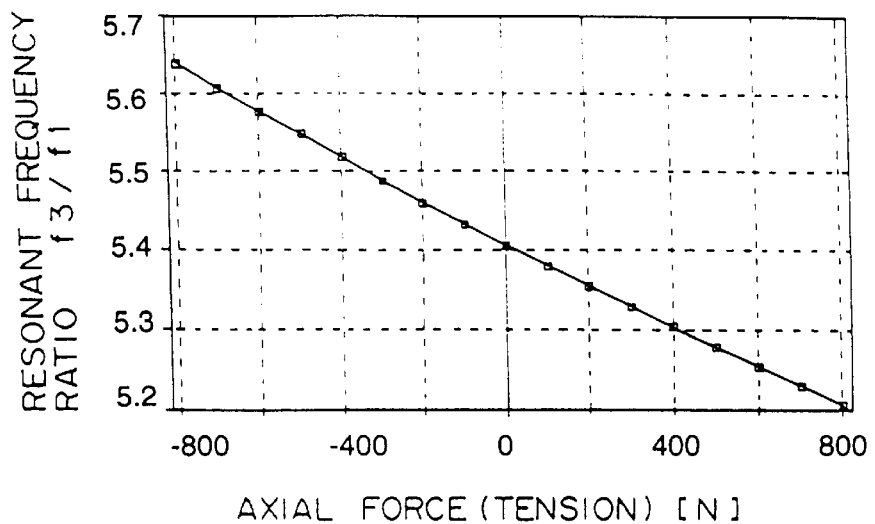
FIG. 4 is a graph showing the relationship between the ratio between the resonant frequency in the primary mode and the resonant frequency in the tertiary mode and the axial force.

FIG. 4 shows an example of the relationship between the ratio of the resonant frequency in the tertiary mode to the resonant frequency in the primary mode and the axial force. "f1" shown in FIG. 4 indicates the resonant frequency in the primary mode, and "f3" indicates the resonant frequency in the tertiary mode. The horizontal axis indicates an axial force, and the vertical axis indicates the frequency ratio (f3/f1) obtained by dividing the resonant frequency in the tertiary mode by the resonant frequency in the primary mode.

Normally, the $\lambda v(T)$ in equation (8) refers to a complicated function, and it is not practical to obtain the axial force from the frequency ratio fr using the function as it is. According to the study of the Inventors, it is more practical to obtain the axial force T using an approximation by a polynomial such as the following equation (10). It is apparent that the approximation using a quadratic function with u set to 2 (u=2) is sufficient in practise.

$$T = \sum_{j=0}^{\mu} (a_j \cdot fr^j) \qquad (10)$$

Where u indicates an integer equal to or larger than 0, and $a_j$ is a coefficient indicating the relationship between the frequency ratio fr and the axial force T.

Figure 5:
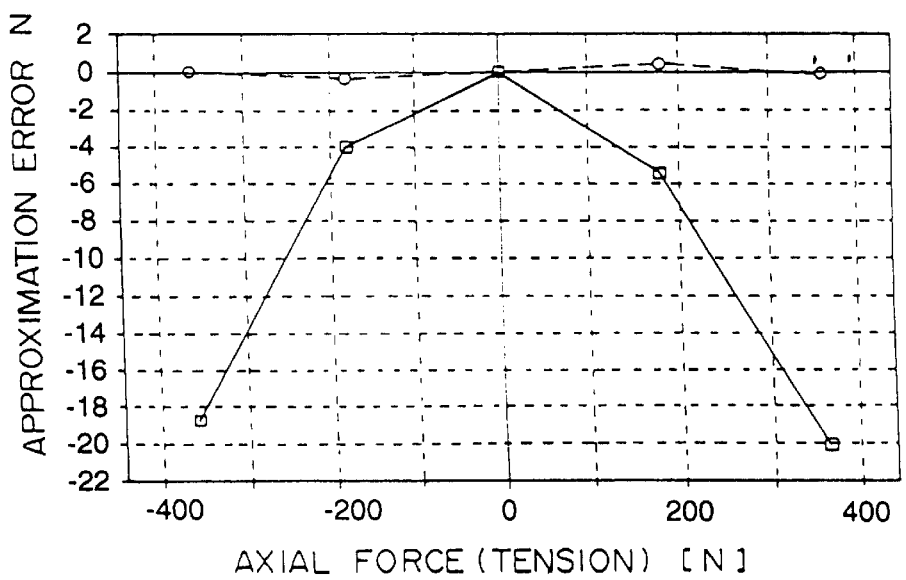
FIG. 5 is a graph showing an approximation error in computing the axial force when the frequency ratio shown in FIG. 4 is approximated using a primary function (linear approximation) and a secondary function.

FIG. 5 shows an approximation error in computing the axial force T when the frequency ratio shown in FIG. 4 is approximated using a linear function (linear approximation) and a quadratic function. The coefficient for use in the approximation using the quadratic function is obtained by the least squares method. As clearly indicated in FIG. 5, a relatively large approximation error is output from the approximation using a linear function, while a very small error is output from the approximation using a quadratic function.

This approximation method is not limited to use in the above described density measurement by equations (6) and (7), but can be applicable to the case where the vibration type measuring instrument using a straight measurement pipe according to the present invention, such as the detecting unit 1 shown in FIG. 2, is used as a Coriolis type mass flow rate meter. When the vibration type measuring instrument is used as a Coriolis type mass flow rate meter, the mass flow rate Qm of the fluid is obtained by the following equation (11) from the phase difference (2α) or time difference Δt between the detection signals of two sensors 6a and 6b, $$\Delta t = 2\alpha/\omega = 4L^3 Qm\eta c(a, T)/EI\eta(a, T) \quad (11)$$

where η indicates a function representing the amplitude at position a along the length of the measurement pipe 2, ω indicates the resonant frequency of the measurement pipe 2, ηc(a) indicates the function of variable (or displacement) amplitude of the straight measurement pipe 2 generated by the stress or reaction from the fluid at a position a along the length of the measurement pipe 2.

As indicated by the equation (11), the phase difference 2α and the time difference Δt change with the axial force T working on the measurement pipe 2. When the axial force T is obtained from the frequency ratio to amend the change, the approximation is practically performed by equation (10) using a quadratic function with u set to 2 (u=2) as described above.

Described below is an example of an density measurement actually performed using the vibration type measuring instrument according to the present invention as shown in FIG. 2. The example shown in FIG. 2 includes only one measuring pipe, but it is obvious that a plurality of measurement pipes can be used for measurement in the same manner.

The resonant frequency ratio used in measuring an axial force is obtained by dividing the resonant frequency in the tertiary mode by the resonant frequency in the primary mode. In measuring a resonant frequency, a resonating system comprises the straight measurement pipe 2, the sensors 6a and 6b for detecting the vibration of the measurement pipe, the driving circuit 8, and the driver 5. The measurement pipe 2 resonates in both primary and tertiary modes by adjusting the frequency band and phase by the driving circuit 8. The signal processing circuit 9' measures both frequencies. Then, the signal processing circuit 9' obtains the resonant frequency ratio by dividing the resonant frequency in the tertiary mode by the resonant frequency in the primary mode, and the temperature sensor 10 measures the temperature of the measurement pipe 2.

FIG. 6 is a table showing the temperature of the measurement pipe 2 and the resonant frequencies in the primary and tertiary modes (f1 and f3 respectively) measured by the measuring instrument according to the present embodiment, the frequency ratio (fr) and fluid density computed by the signal processing circuit 9', the true value of the fluid density, and the error between the computed density and the true value. Data Nos. 1–3 are experimental values obtained when fluids having different densities are run in the measurement pipe 2. They are measured in a way that the detecting unit 1 can be maintained at a constant temperature, and in a way that no axial force is generated in the measurement pipe. As a result, the resonant frequency ratio of data Nos. 1–3 indicates an approximately constant value. Data Nos. 4–7; indicate values obtained by altering the axial force working on the measurement pipe, with the density of the fluid in the measurement pipe kept constant. In this case, the frequency ratio changes with the axial force.

The procedure of obtaining the density from the measured values f1 and f3 of the resonant frequency of data Nos. 1–7 and the temperature of the measurement pipe is described as follows.

First, the axial force is obtained by equation (10) based on the frequency ratio fr. Each value is different from the value shown in FIG. 4, but the axial force T can be successfully approximated using a quadratic function of the frequency ratio fr (u=2). A practical equation (12) is described as follows.

$$T = a_2 fr^2 + a_1 fr + a_0 \quad (12)$$

($a_2$:1692.2, $a_1$:−20338.7, $a_0$:59229.3)

Next, the constants A, B, and C are determined by equation (7) for computation of fluid density. When the constants are determined, data Nos. 1, 2, and 4 are used. In each case, ternary linear simultaneous equations are generated using the constants A, B, and C as unknown elements by substituting in equation (7) the axial force T obtained by equation (12); a value obtained by amending, using the temperature of the measurement pipe, a thermal change of Young's modulus E and a thermal expansion change in I, L, and Si; a true value ρw of fluid density; and a resonant angular frequency ω. Thus, the constants A, B, and C are obtained by solving the above described simultaneous equations. At this time, either f1 or f3 can be used for the angular frequency ω (=2πf1 or 2πf3). Since all data should be consistent, f3 is adopted in this embodiment.

The data Nos. 1, 2, and 4, which seem to be independent, are selected from among the seven data groups and used in determining the constants. As a result the following constants are output.

A=0.0155343
B=0.0004201
C=−0.000023

After the constants A, B, and C in equation (7) are determined, the measurement results of data Nos. 1–7 are substituted in equation (7) to compute the density, and an error is obtained by comparing the density with a true value. In rows 2–4 in the table of FIG. 6, data Nos. 1, 2, and 4 are used in determining the constants A, B, and C, and therefore output an error of 0. With other data, the error is equal to or smaller than 0.001 [g/cm$^3$], which shows that precise measurement results can be obtained.

According to the present invention, a density computation is performed by equation (6) and a precise measurement can be made by amending, by a simple computation, the influence of axial force and added mass, using a simple, rigid, and convenient measuring instrument including a straight measurement pipe as shown in FIG. 2. The computation can be more easily performed by explicitly solving equation (6) for the density ρw and collectively performing integration and summation (Σ) and substituting for the constants A, B, and C.

Furthermore, a measurement can be made at a higher precision by amending the constants A, B, and C based on actual data through the use of simultaneous equations and the method of least squares. The measurement can be made accurately for a mass production using the axial force obtained from the resonant frequency ratio in operations. In this case, it is desired to use the ratio of the resonant frequency in the primary mode to that in the tertiary mode or the ratio of the resonant frequency in the tertiary mode to that in the quinary mode. Operations can be practically performed by approximating the axial force as a polynomial of a resonant frequency ratio as indicated by equation (10). In this case, a quadratic polynomial can be used to further simplify the operations.

Described below is the second embodiment of the present invention.

Figure 7:
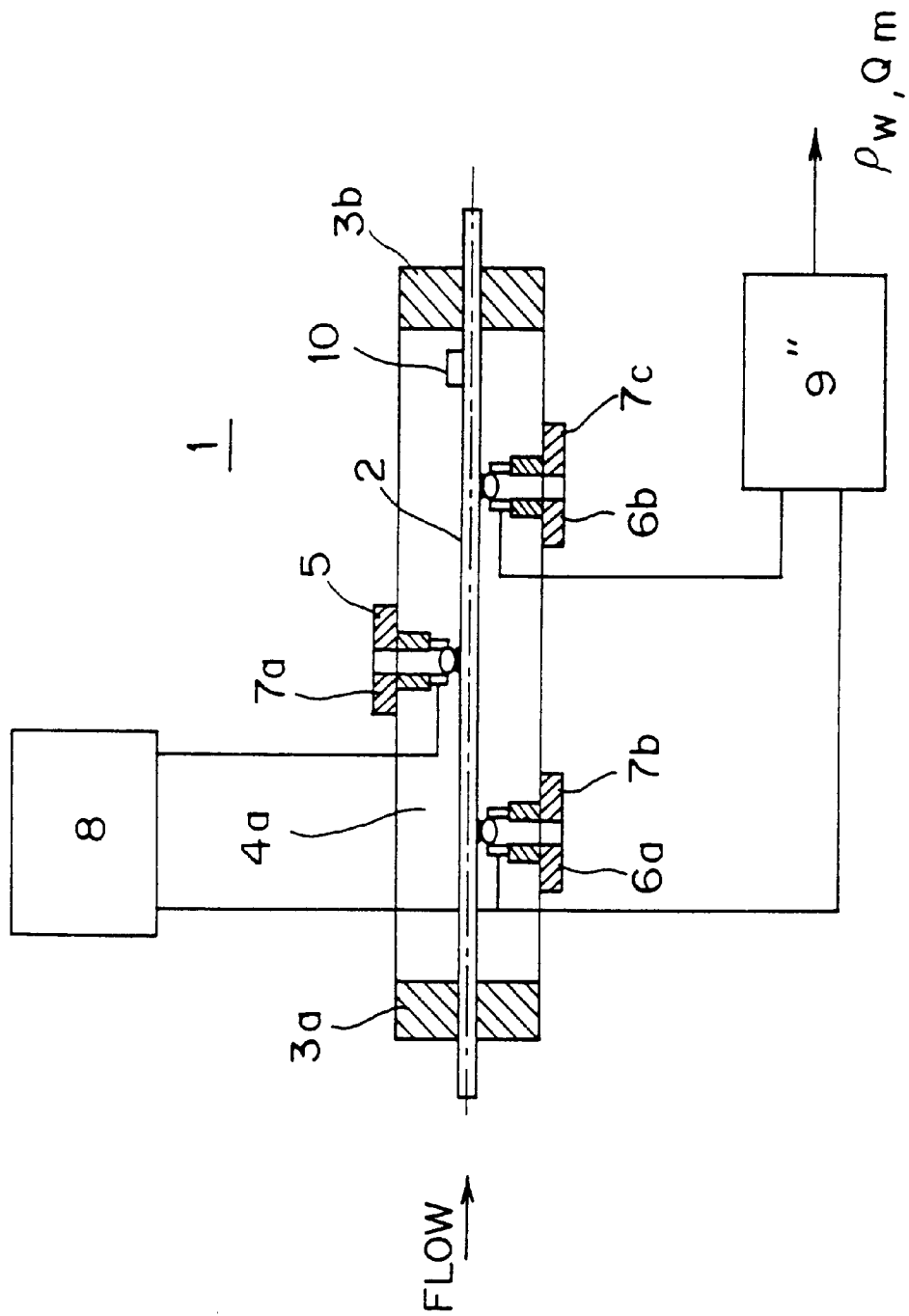
FIG. 7 shows the configuration of the second embodiment of the vibration type measuring instrument according to the invention.

FIG. 7 shows the second embodiment of the vibration type measuring instrument according to the present invention. Same elements used in FIGS. 1A, 1B, and 2 are assigned the same reference numbers in this embodiment, and the detailed descriptions are omitted here.

As shown in FIG. 7, the vibration type measuring instrument according to the second embodiment comprises the detecting unit 1, driving circuit 8, and signal processing circuit 9". The detecting unit 1 and driving circuit 8 are the same as those in FIGS. 1A, 1B, and 2. The signal processing circuit 9" obtains the resonant frequency of the measurement pipe 2 based on the signal from the sensors 6a and 6b, and computes the fluid density ρw and the mass flow rate Qm using the resonant frequency by the method described below.

According to the second embodiment, the iterative method defined below is adopted.

Assume that the following equation (13) is expressed defined in a closed area (range) R=[a, b] using a given function f(z).

$$z = f(z) \quad (13)$$

The solution of the equation (13) is the convergence value of the sequence $\{z_n\}$ inductively generated by the initial value $z_0$ arbitrary selected in the above described closed area R and the following equation (14).

$$z_n = f(z-1) \quad (14)$$

(n=1,2, ... )

When the following conditions i)., ii), and iii) are satisfied in the above described method, it is proved that the equation (13) has an only one solution in the closed area R, and the sequence $\{z_n\}$ converges into only one solution.

i) f(z) is consecutive (continuous) in the closed area R.
ii) f(z)∈R for all z∈R.
iii) The following equation (15) is expressed for all $z_1$, $z_2$∈R.

$$|f(z_1)-f(z_2)| < |z_1-z_2| \quad (15)$$

The definition, theorem, and proof of the above described iterative method are described in, for example, "The Basic Value Analysis" (written by P. Henritch, translated by Shin Ichimatsu, et al., and published by Baifukann) on pages 59 through 65.

According to the study of the Inventors, the above described conditions i), ii), and iii) are satisfied by the following equation (17) (where T' remains as containing ρw as a variable) obtained by explicitly solving the following equation (16) converted from the equation (6) above for the fluid density ρW. Therefore, the sequence $\{\rho w_n\}$ always converges into ρw, which is the only solution, by applying the above described iterative method to the equation (17). Thus, this method successfully obtains the fluid density ρw.

$$\omega_i^2 = \left\{ EI \int_0^L (d^2y/dx^2)^2 dx - T' \int_0^L y(d^2y/dx^2) dx \right\} / \quad (16)$$

$$\left\{ (\rho wSi + \rho tSt) \int_0^L y^2 dx + \sum_{k=1}^M (mk \cdot yk^2) \right\}$$

$$\rho w_n = (AEI/\omega_i^2 L^4 Si) + (BT'(fr, \rho w_{n-1})/\omega_i^2 L^2 Si) + (C/LSi) \quad (17)$$

where:
E indicates the Young's modulus E of the measurement pipe 2,
I indicates the cross-sectional secondary moment of the measurement pipe 2,
T' indicates the axial force (=T'(fr, ρw)) working on the measurement pipe 2,
ρw indicates the density of the fluid,
ρt indicates the density of the measurement pipe 2,
Si indicates the cross-sectional area of the hollow portion of the measurement pipe 2,
St indicates the actual cross-sectional area of the measurement pipe 2,
L indicates the length of the measurement pipe 2,
x indicates a position x in the axial direction along the measurement pipe 2 (x=0 at one end of the measurement pipe 2 and x=L at the other end of the measurement pipe 2),
y indicates the vibration amplitude (a function containing the variable x) of the measurement pipe 2 at the position x,
M indicates the number of masses added to the measurement pipe 2,
mk indicates the k-th added mass (k=1 through
yk indicates the vibration amplitude of the k-th added mass (k=1 through M), and The density ρw obtained by equation (17) is represented as a function such as E, I, T', Si, etc. as shown by the equations (18) and (19), and T' contains ρw as a variable.

$$\rho w = g(E,I,T'(fr,\rho w), Si, \ldots) \quad (18)$$

$$\rho w_n = g(E,I,T'(fr,\rho w_{n-1}), Si, \ldots) \quad (19)$$

The measurement precision of the fluid density can be improved by amending the influence on the measurement of the fluid density by the axial force T, by obtaining the density by the above described equations (16) and (17).

When the vibration type measuring instrument according to the present embodiment is used as a Coriolis type mass flow meter, a mass flow rate is measured by the method according to the first embodiment by obtaining the axial force T using the above described function T (fr, ρw) from the fluid density ρw and frequency ratio fr obtained by the above described method. Therefore, the amendment of the measurement value (phase difference) can be made by the axial force T with precision when the mass flow is obtained.

A problem with the above described iterative method is the convergence speed. According to the study of the Inventors, the convergence is normally obtained very quickly when the iterative method is applied to the equation (17). In a later described example, a convergence value is obtained after two or three iterations with practically acceptable precision. Therefore, the time required for repetitive operations can be considerably shortened.

Although equation (16) contains an integration term, the integration term does not have to be computed each time it appears. It can be replaced with a predetermined constant without any practical problem. Equation (17) is obtained by collectively replacing the integration term and summation (Σ) term in equation (16) with the constants A, B, and C after explicitly solving equation (16) for the density ρw (with the axial force T left as containing ρw). Using the predetermined constants A, B, and C, an acceptable precision can be obtained. In this method, the format of the equation can be simplified and operations can be easily performed.

It is not practical to obtain the constants A, B, and C in equation (17) through actual operations, because there can be a dimension error, residual stress, etc., remaining in the detecting unit 1 of the vibration type measuring instrument as shown in FIG. 7 from the assembly of the apparatus. Therefore, it is desirable to actually measure the density and then amend the constants to furthermore improve the density measurement precision. The amendment can be made as follows.

In a certain state, when the values of ρw, E, I, ω, L, Si, and T are measured and substituted in equation (17) (ρw is substituted for $\rho w_n$ and $\rho w_{n-1}$), an equation is expressed with the constants A, B, and C set as unknown numbers. Thus, three equations are expressed after measurements are made three times in different states (with the density, temperature, axial force, etc. changed). Solving these equations as simultaneous equations uniquely obtains the three unknown numbers. Since this method determines the constants A, B, and C using actually measured values, the constants are appropriate for the measuring instrument, thereby improving the measurement precision. However, unless the simultaneous equations are independent, the unknown numbers A, B, and C cannot be uniquely determined. If they are only slightly independent, the obtained numbers A, B, and C may contain large errors. Therefore, it is desired that measurements are made in three more significantly independent states.

As described above, the convergence speed is a problem with the iterative method. The convergence speed is determined by the way the initial value $\rho w_0$ is selected. It is normally certain that the convergence can be quickly attained when an operation is started from an initial value close to a convergence value.

Generally, the fluid density does not greatly fluctuate unless the type of fluid is changed or the states are suddenly switched. Therefore, it is probable that the previous density measured value is close to the current density measured value. Assuming that an appropriate initial value $\rho w_0$ is selected as the first measurement after the measuring instrument is turned on, the computation by the above described iterative method quickly converges on an average by setting the previous density measured value as a new initial value $\rho w_0$ for the next measurement.

Up to the current step of the iterative method, an operation is performed until the sequence $\{\rho w_n\}$ converges and the convergence value is determined as a density measured value ρw. However, the operation is not actually performed until the sequence converges with an integer v (equal to or larger than 1) set as an iterative time (number) for computations. A value obtained by performing the iterative computations v times can be a density measured value ρw. The features of this method are:

(1) The time required for performing operations can be shortened because the time of operations can be reduced and it is not necessary to determine a convergence.

(2) Since the quantity of operations is limited, the measurement cycle can be kept constant.

(3) Since the measured value is not a convergence value, measurement error increases.

Regarding item (3) above, an acceptable precision can be attained by applying the previous density measured value as an initial value as described above. Therefore, this method has an advantage when it is applied to an actual vibration type measuring instrument. Especially when a convergence is attained in two or three iterative operations, v=1 is practically acceptable.

Normally, the above described axial force T (fr, ρw) becomes a much complicated function and is very difficult to use in operations. However, the function fr (T', ρw) obtained by solving T' (fr, ρw) for fr can be processed as a separated variable as in the following equation (20).

$$fr=fr(T',\rho w)=ft(T')\cdot fd(\rho w) \qquad (20)$$

Equation (20) indicates that the frequency ratio fr can be represented by a product of the function ft (T') indicating the influence of the axial force T' and the function fd (ρw) indicating the influence of the density ρw of a fluid.

Rearranging the equation (20), the following equation (21) is obtained.

$$ft(T')=fr/fd(\rho w) \qquad (21)$$

The right side of equation (21) indicates that the influence of the fluid density ρw on the frequency ratio fr is canceled by dividing the frequency ratio fr by the function fd (ρw) indicating the influence of the fluid density ρw. Additionally, assuming that the inverse function of ft (T') is Tr, the following equation (22) can be expressed.

$$T'=T(fr,\rho w)=Tr\{fr/fd(\rho w)\} \qquad (22)$$

Equation (22) indicates the axial force as a function of fr/fd (ρw) obtained by canceling the influence of the fluid density ρw on the frequency ratio fr.

According to the first embodiment, the axial force is represented as a function of only the frequency ratio fr in the form of T (fr). The function T (fr) normally indicates a complicated form, but the first embodiment realizes a practically acceptable precision by approximating the function by a polynomial of fr.

It has also been proved that a practically acceptable precision can be obtained when the function Tr (fr/fd (ρw)) indicating the axial force T' represented by the right side of the above equation (22) is approximated using a polynomial. The approximation equation is practically represented by the following equation (23), $$Tr\{fr/fd(\rho w)\} = \sum_{j=0}^{p} [bj\{fr/fd(\rho w)\}^j] \qquad (23)$$

where p indicates an integer equal to or larger than 0, and
bj is a coefficient indicating the relationship between $\{fr/fd(\rho w)\}^j$ and the function Tr.

An approximation using a quadratic polynomial (p=2) has proved to be acceptable.

Similarly, it is also been proved that a practically acceptable precision can be obtained by a polynomial approximation for the function fd (ρw) indicating the influence of the fluid density ρw on the above described frequency ratio fr. The approximation is practically represented by the following equation (24), $$fd(\rho w) = \sum_{j=0}^{\mu}(aj \cdot \rho w^j) \quad (24)$$

where u indicates an integer equal to or larger than 0, and aj is a coefficient indicating the relationship between the fluid density ρw and the function fd.

This approximation using a quadratic polynomial (p=2) or a cubic polynomial (p=3) has proved to be acceptable according to the dimension of the detecting unit 1 shown in FIG. 7.

Thus, the function T'(fr,ρw) is represented by an easily computable form, and a practically acceptable computation precision can be obtained by approximating the function T (fr,ρw) by the form of the function Tr(fr/fd (ρw)), by approximating the function Tr (fr/fd (ρw)) by a polynomial of fr/fd (ρw), and by approximating the function fd (ρw) by a polynomial of ρw.

After further investigation, it has been proved that, in the detecting unit 1 shown in FIG. 7, the function fd (ρw) indicating the influence of the fluid density ρw on the above described frequency ratio fr may not approximate using a quadratic or cubic polynomial. In such a case, the value of the function fd (ρw) is measured for the fluid density ρw of several types of fluids, and a series of lines fd (ρw) interpolate data from the measured values so that a computation can be easily made and a practically acceptable computation precision can be obtained.

As described above, the axial force T' is not only a function of the frequency ratio fr, but it depends on the fluid density ρw as a form of T (fr, ρw), by the influence of an added mass such as the driver 5, sensors 6a and 6b, and temperature sensor 10 provided for the measurement pipe 2 shown in FIG. 7. This indicates that the function T(fr·ρw) or the function fd(ρw) indicating the influence of the fluid density ρw on the frequency ratio fr, alters with the above described added masses. As also described above, an equation normally converges very quickly when the iterative method is applied to equations (17) and (19) as in the present invention because the slope of f(z) in the above described equation (13) is much smaller than 1. Generally, the smaller the slope of f(z) is, the more quickly the iterative method converges. For an example, if the slope of f(z) is zero and the f(z) is a constant, then the equation converges after one operation.

Thus, the iterative method can quickly converge by reducing the slope of the right side of the above described equation (17) or (19) (corresponding to f(z) of equation (13)) to ρw, by adjusting the form of the above described function T (fr, ρw) or fd (ρw) while altering an added mass. Normally, the slope of the T (fr,ρw) or fd (ρw) should be reduced to reduce the slope of the right side of equation (17) or (19) to ρw. A practical method of altering the added mass is to change the weight, mounting position, or the number of the driver 5, sensors 6a and 6b, and temperature sensor 10 shown in FIG. 7. Otherwise, other added masses can be mounted with weight, mounting position, or number approximately adjusted.

Normally, the straight measurement pipe 2 as shown in FIG. 7 has an enormous number of vibration modes such as shown in FIG. 3 as described above. All the above described methods can be applicable at the resonant frequency ratio fr between any two modes. However, when a resonant frequency is actually measured, the frequency of the straight measurement pipe 2 is measured by making the straight measurement pipe 2 resonate, or the transmission function is measured by actually sweeping the resonant frequency. In any case, an odd-order mode is desired so that the center of the measurement pipe probably corresponds to an antinode of the vibration when the driver 5 is mounted at the center of the straight measurement pipe 2 as indicated by the detecting unit 1 shown in FIG. 7. Additionally, excitation and measurement can be more easily realized at a lower frequency in a lower-order mode. After a close study, it has been proved that the resonant frequency ratio between the primary and tertiary modes (primary/tertiary, or tertiary/primary) or between the tertiary and quinary modes (tertiary/quinary, or quinary/tertiary) is appropriate.

Described below is a density measurement actually made using the vibration type measuring instrument according to the second embodiment. The detecting unit 1 of the vibration type measuring instrument shown in FIG. 7 comprises a measurement pipe, but the detecting unit 1 can comprise a plurality of measurement pipes.

The resonant frequency ratio fr used in an axial force measurement is obtained by dividing the resonant frequency in the tertiary mode by the resonant frequency in the primary mode. In measuring a resonant frequency, the measurement pipe 2 is made to resonate in both tertiary and primary modes using a resonating system comprising the straight measurement pipe 2, sensors 6a and 6b for detecting the vibration of the measurement pipe, driving circuit 3, and driver 5, by adjusting the frequency band and phase by the driving circuit 8. After measuring both frequencies, the signal processing circuit 9" obtains the resonant frequency ratio by dividing the resonant frequency in the tertiary mode by that in the primary mode, and performs an amending process according to the temperature of the straight measurement pipe 2 measured by the temperature sensor 10.

The relationship between the axial force and the resonant frequency ratios between the primary and tertiary modes is described in explaining the first embodiment by referring to FIG. 4.

FIG. 8 is a table showing the fluid density ρw and f(ρw) obtained by applying the function of the above described equation (17) to the data processing through the measuring instrument shown in FIG. 7. FIG. 9 is a graph showing the relationship between the fluid density ρw and f(ρw). In this graph, the density measurement range is 0.4 through 3.0 g/cc. The f(ρw) corresponds to the right side of equation (17). The Tr (fr/fd (ρw)) in equation (22) is used as the axial force T (fr, ρw) in equation (17). Using the equation in which u=2 is applied to the above described equation (24), the fd (ρw) is approximated using a quadratic function shown in equation (25). Thus, operations can be more easily performed.

$$fd(\rho w) = a2 \cdot \rho w^2 + a1 \cdot \rho w + a0 \quad (25)$$

a2: −0.0012384
a1: 0.0038639
a: 0.997214

To make the above described iterative method converge into only one solution, fd (ρw) should satisfy the above described conditions i), ii), and iii). It is apparent that the fd (ρw) satisfies the conditions i) and ii). Considering the condition iii), the above described equation (15) can be transformed as shown in the following equation (26) with the function fd'(ρw) obtained by once differentiating the fd (ρw) regarded as a sequence.

$$|fd'(\rho w)| < 1 \quad (26)$$

According to FIG. 9 and the table in FIG. 8, the fd(ρw) indicates the slope of only 1/100, thereby satisfying the above described equation (26). Therefore, the fd (ρw) satisfies the conditions i), ii), and iii), and the ρw necessarily converges into only one solution according to the above described iterative method.

FIG. 10 is a table showing the result of checking the speed of the convergence of the fd (ρw). On the table, the values of the density and f (ρw) are obtained based on the above described iterative method using water (density 0.997 g/cc) as a fluid to be measured.

In the table shown in FIG. 10, the values are divided into four blocks by blank rows. Each of the leading values in the respective blocks is the initial value $\rho w_0$ of the ρw used in the iterative method. The f(ρw) in the adjacent column in the row is the result, that is, $\rho w_1$, obtained by substituting the initial value $\rho w_0$ in equation (17). The $\rho w_1$ is in the column below that containing $\rho w_0$. Using the $\rho w_1$, the $\rho w_2$ is computed. FIG. 10 shows the five-times repetition of the computation, and up to $\rho w_5$ has been obtained. FIG. 10 shows that ρw converges after at most two times of repetitive computations for each initial value. Thus, the convergence is normally reached quickly if the iterative method is applied to equation (17) because, it is assumed, the slope of the f (ρw) is much smaller than 1 as shown in FIG. 9. According to the table of FIG. 10, the convergence is reached more quickly as the initial value is closer to the convergence value. Therefore, the density can converge quickly when the previous convergence value (measured value) is used as an initial value.

Figure 11:
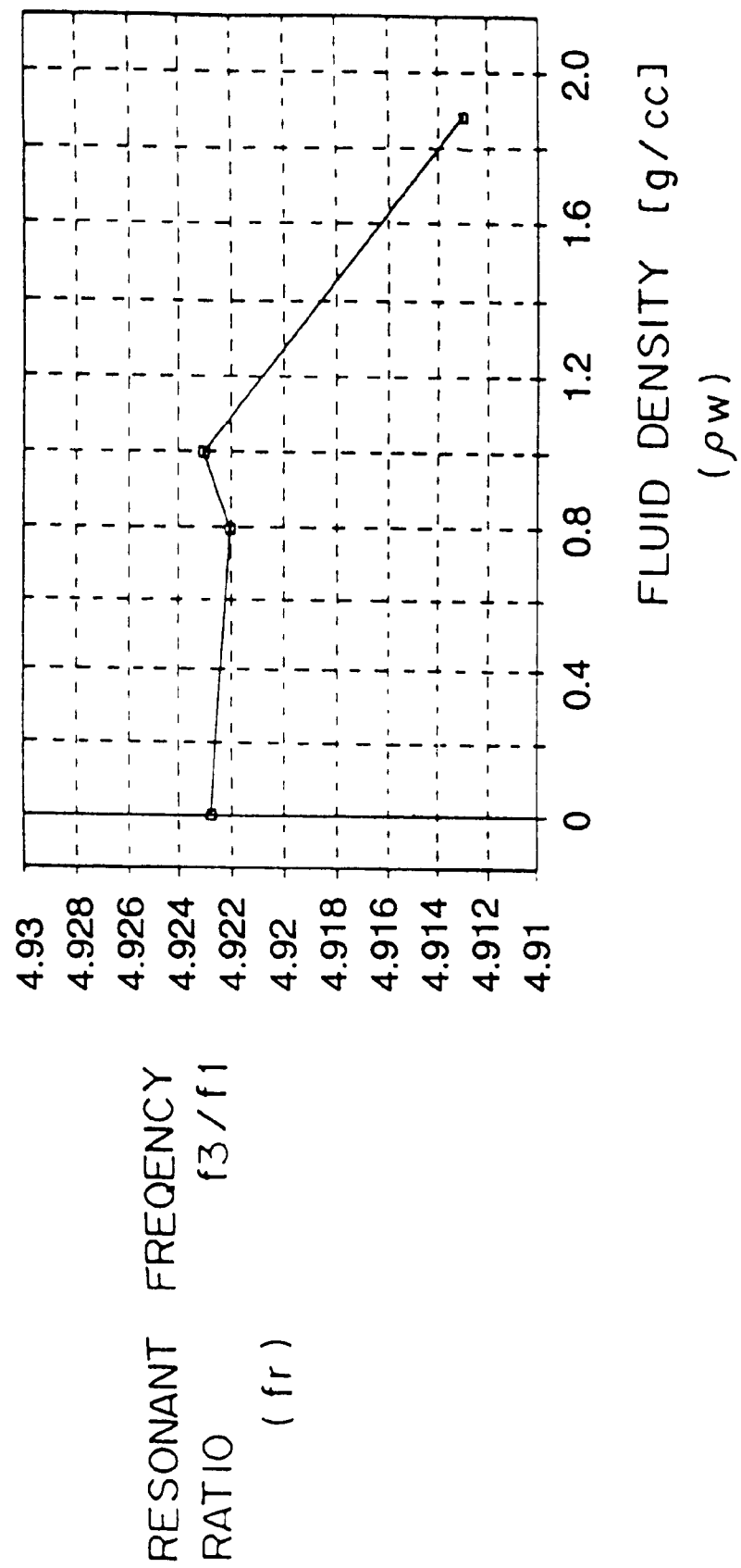
FIG. 11 is a graph showing the relationship between the resonant frequency ratio of the tertiary mode to the primary mode and the fluid density.

FIG. 11 shows the relationship between the fluid density ρw and the resonant frequency ratio fr (f3/f1) between the tertiary and primary modes. f1 indicates the resonant frequency in the primary mode, and the f3 indicates the resonant frequency in the tertiary mode.

In the example shown in FIG. 11, the resonant frequency ratio fr alters to the format in which it cannot easily approximate relative to the density ρw using a polynomial containing a quadratic or cubic function. Therefore, the function fd (ρq) indicating the influence of the density ρw on the resonant frequency ratio fr cannot be easily represented by a polynomial containing ρw in equation (24). As a result, the lines interpolating values in measured points (□) are referred to as fd (ρw) as shown in FIG. 11. In this case, since the fd (ρw) satisfies the convergence conditions i), ii), and iii) of the above described iterative method, the ρw necessarily converges into only one solution.

FIG. 12 is a table showing the data relating to the density measurement. The data in this table indicates the convergence of the iterative method when the above described lines are used.

The table shows the result obtained by computing the density of four types of fluids (corresponding to Nos. 1 through 4). Air is used for the fluid No. 1 for easier amendment. The density measurement range is 0.4 through 3.0 g/cc. The columns on the right of each data number contain an actually measured value of the fluid density, an initial value, a computed density value, and an error value in this order. The density is computed using two types of initial values for each fluid.

The first block of each data number on the table shown in FIG. 12 contains the result obtained using an actually computed value as the initial value $\rho w_1$. The second block contains the result obtained using the value indicating the largest difference from the actually measured value in the density measurement range (the value that implies the last convergence) as the initial value $\rho w_0$. In each block, the first row contains the computed value $\rho w_1$, and the second row contains the computed value $\rho w_2$. The error indicates the difference between the actually measured value and the computed value. According to the table of FIG. 12, the iterative method converges to a correct solution in all computations. Since the convergence is reached in at most two operations, the method proves to converge quickly.

The table of FIG. 13 indicates the fluid density, the measured value of the temperature of a measurement pipe obtained while changing the axial force T working on the measurement pipe, the measured results of the resonant frequencies f1 and f3 in the primary and tertiary modes, and the result obtained by computing the fluid density by equation (17) based on the above described measurement results.

In the table of FIG. 13, the data Nos. 1 through 4 indicate the measurement results obtained by filling the measurement pipe with fluids of different density values. At this time, the measuring instrument shown in FIG. 7 is kept at a predetermined temperature, and no axial force works on the measurement pipe. Therefore, the change in the resonant frequency ratio fr represented by the rate of change of the data of Nos. 1 through 4 depends on the change in the density. In this measurement, the change in the resonant frequency ratio is amended by representing the above described fd (ρw) by a series of lines. Among the data, the change in the resonant frequency ratio fr of the data No. 4 is remarkable.

The data Nos. 5 through 9 indicate the measurement results obtained by altering the value of the axial force working on the measurement pipe with the density of the fluid in the measurement pipe kept constant. The data indicate that the axial force changes the frequency ratio fr.

The density is computed based on the measured values f1 and f3 of data Nos. 1 through 9 as follows. First, the fd(ρw) is represented by the above described lines. Then, the axial force T is expressed by the following equation (27) using the fr/fd(ρw) with the p in equation (23) set to 2 (p=2).

$$T = b2 \cdot \{fr/fd(\rho w)\}^2 - b1 \cdot fr/fd(\rho w) - b0 \quad (27)$$

where b2=25332.2 b1=−283428 b0=781360

Next, the constants A, B, and C are determined by equation (17) as a density computation equation. In this example, the axial force T obtained by equation (27); the values obtained by amending, using the temperature of the measurement pipe, the temperature change of the Young's modulus E and the change in I, L, St, and Si by thermal expansion for each case using three types of data, that is, data Nos. 1, 5, and 7; the actually measured value ρw of the fluid density; and the resonant angular frequency ω1, are substituted in equation (17) to produce simultaneous linear equations containing three unknown numbers A, B, and C. Each of the constants is obtained by solving the simultaneous equations. The angular frequency ω1 is ω=2πf1 or 2πf3. In this case, either f1 or f3 can be selected for the entire data. In this example, the f3 is selected.

The data used in determining the constants are selected because they are highly independent. As a result, the following values are obtained.

A=0.364216

B=0.00284406

C=−0.0000909489

Thus, after determining the constants A, B, and C in equation (17), the density is computed by the iterative method by substituting the measurement results of data Nos. 1 through 9 in equation (17). The obtained density is compared with the actually measured value to compute the error. By referring to the second through fourth rows of the table of FIG. 13, the data Nos. 1, 5, and 7 are used in determining the constants A, B, and C, and therefore naturally output an error value of 0. Other data also indicate an error equal to or smaller than 0.001 g/cc, thereby obtaining an acceptable measurement precision.

The table of FIG. 14 indicates the result of computing the density by equation (7) for comparison with the measured values on the table of FIG. 13. Equation (7) is different from equation (17) in that the axial force is represented by T (fr) without considering the density dependency to obtain the axial force T, and that the iterative method is not utilized.

By referring to the table of FIG. 14, the error 0.004 g/cc of the computation result of data No. 4 indicating a large change in the resonant frequency ratio fr is four times as large as the value shown in FIG. 13. The error occurs because T (fr) is used regardless of the density dependency in obtaining the axial force T. The error is reduced by the iterative method by representing the axial force T as, for example, T (fr, ρw) in consideration of the density dependency as shown in the table of FIG. 13.

Figure 15:
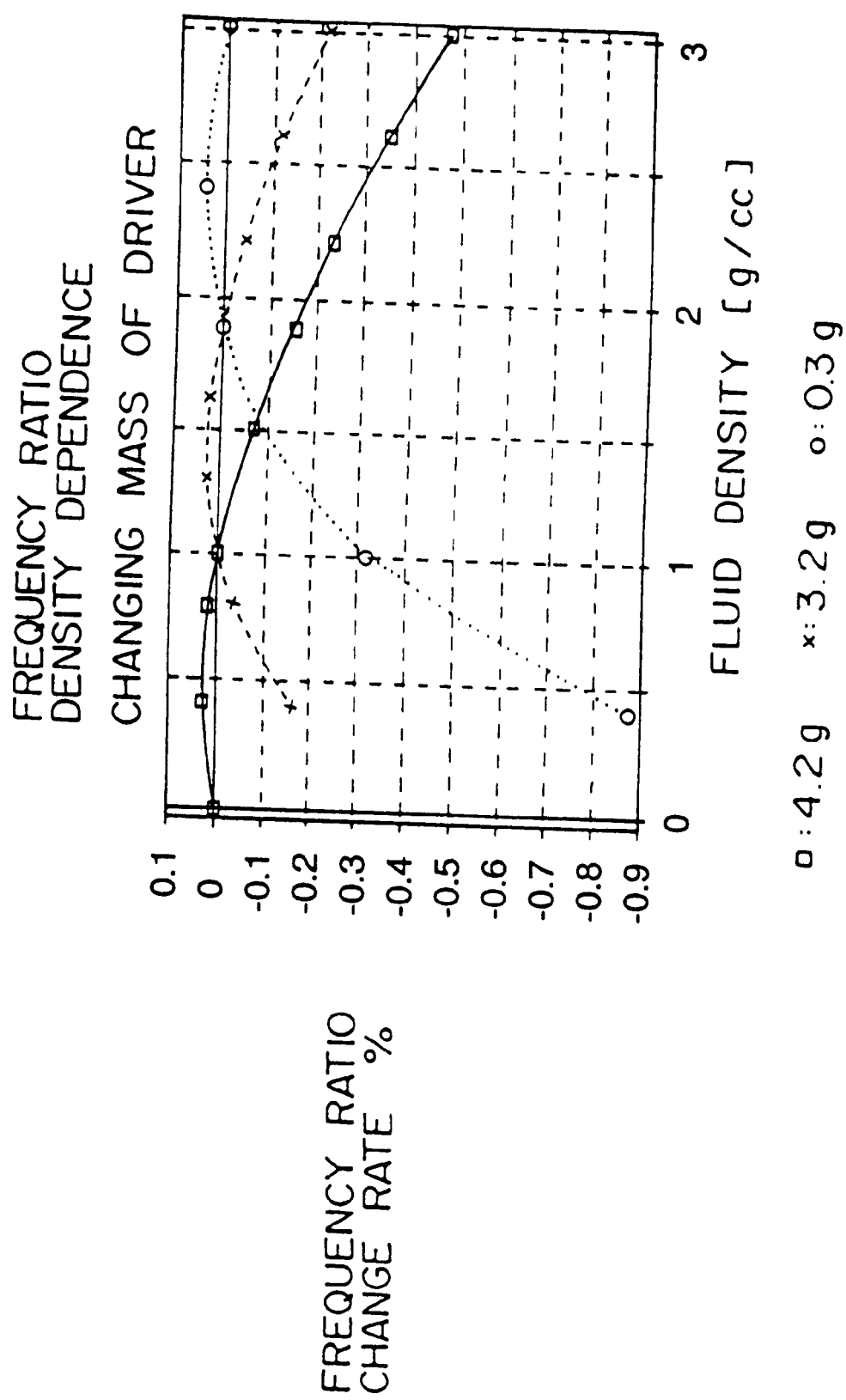
FIG. 15 is a graph showing the dependency of the frequency ratio fr on the fluid density ρw.

FIG. 15 shows an example of the frequency ratio density dependency when the dependency (function fd (ρ, V)) of the frequency ratio fr on the fluid density ρw is changed by altering an added mass to the measurement pipe.

FIG. 15 actually shows the dependency of the frequency ratio fr on the fluid density ρw when the mass of the driver 5 shown in FIG. 7 is changed to 4.2 g (corresponding to □), 3.2 g (corresponding to +), and 0.8 g (corresponding to O). By altering the added mass, the dependency of the frequency fr on the fluid density ρw, that is, the form of the function fd (ρw), or the form of the axial force T (fr, ρw), can be changed.

Normally, the smaller the slope of f(z) in equation (13) is, the more quickly the convergence is reached in the iterative method. Therefore, when T (fr, ρw) or fd (ρw) is changed to reduce the slope in equation (17) or (19), the convergence can be quickly reached. Generally, if the slope to the ρw of T (fr, ρw) or fd (ρw) is reduced, the slope of the right side of equation (17) or (19) is also reduced. In FIG. 15, the graph indicating the density 3.2 g, which is plotted with (+), is considered to converge first.

According to the present invention, the influence of the change in fluid density on the density measurement and axial force measurement can be amended by applying equation (17) and the iterative method to a density operation, thereby realizing a high-precision measurement of density and axial force. Operations can be furthermore easily performed by explicitly solving equation (16) for the density ρw, and applying the iterative method to equation (17) in which the integration term and summation (Σ) are collectively replaced with the three constants. When an iterative method is used, the convergence can be quickly reached by performing an operation using the previous density measured value as the next initial value. The computation can be terminated after repeating operations a predetermined number of times without continuing the computation until the calculated value converges. Thus, the amount of computation can be limited and a practically acceptable precision can be obtained.

Furthermore, according to the present invention, an easy computation format can be determined for the axial force T (fr, ρw), and the convergence can be quickly reached by adjusting the mass added to the measurement pipe. The resonant frequency ratio can be easily measured with the resonant frequency ratio of the primary to tertiary mode or the tertiary to quinary mode.

What is claimed is:

1. A vibration type measuring instrument for measuring at least one of mass flow rate and density of a fluid flowing through a straight measurement pipe by vibrating the pipe, comprising:

a straight measurement pipe;

a vibration detecting means for detecting vibration of said measurement pipe; and signal processing means for obtaining a resonant angular frequency ω and axial force T of said measurement pipe based on a detection signal of said vibration detecting means, and obtaining a density ρw of the fluid flowing through said measurement pipe based on a following equation (E1) using the obtained resonant angular frequency ω and the axial force T, $$\omega^2 = \left\{EI\int_0^L (d^2y/dx^2)^2 dx - T\int_0^L y(d^2y/dx^2)dx\right\} / \left\{(\rho w Si + \rho t St)\int_0^L y^2 dx + \sum_{k=0}^n (mk \cdot yk^2)\right\} \quad (E1)$$

where E indicates the Young's modulus of said measurement pipe, I indicates a cross-sectional secondary moment of said measurement pipe, Si indicates a cross-sectional area of a hollow portion of said measurement pipe, ρt indicates a density of said measurement pipe, St indicates an actual cross-sectional area of said measurement pipe, L indicates a length in an axial direction of said measurement pipe, x indicates a position in the axial direction of said measurement pipe, y indicates a vibration amplitude of said measurement pipe at position x, n indicates a number of masses added to said measurement pipe, mk indicates the mass of a k-th added mass, and yk indicates a vibration amplitude of the k-th added mass.

2. The vibration type measuring instrument according to claim 1, wherein said signal processing means calculates the density ρw of the fluid flowing through said measurement pipe based on a following equation (E2) obtained by solving the equation (E1) for the density ρw using constants A, B, and C determined by a vibration form of said measurement pipe and a mass added, $$\rho w = (AEI/\omega^2 L^4 Si) + (BT/\omega_2 L^2 Si) + (C/LSi) \quad (E2).$$

3. The vibration type measuring instrument according to claim 2, wherein said constants A, B, and C are determined by solving simultaneous equations of three different equations obtained by substituting in the equation (E2) three sets of values, obtained in three different states, of the density ρw of the fluid, the Young's modulus E of said measurement pipe, the cross-sectional secondary moment I of said measurement pipe, the resonant angular frequency ω and axial force T of said measurement pipe, length L along the axial direction of said measurement pipe, and a cross-sectional area Si of the hollow portion of said measurement pipe.

4. The vibration type measuring instrument according to claim 2, wherein said constants A, B, and C are determined by a least squares method in a way that an error among at least three equations is minimized after generating at least three different equations by substituting in the equation (E2) three sets of values, obtained in at least three different states, of the density ρw of the fluid, the Young's modulus E of said measurement pipe, the cross-sectional secondary moment I of said measurement pipe, the resonant angular frequency ω and axial force T of said measurement pipe, length L along the axial direction of said measurement pipe, and a cross-cross-sectional area Si of the hollow portion of said measurement pipe.

5. The vibration type measuring instrument according to claim 1, wherein
   said signal processing means obtains the axial force T based on a ratio between a resonant frequency of a first vibration mode of said measurement pipe and a resonant frequency of a second vibration mode of said measurement pipe.

6. The vibration type measuring instrument according to claim 5, wherein
   said first and second vibration modes are respectively the primary and tertiary vibration modes of said measurement pipe.

7. The vibration type measuring instrument according to claim 5, wherein
   said first and second vibration modes are respectively a tertiary and a quinary vibration modes of said measurement pipe.

8. The vibration type measuring instrument according to claim 5, wherein
   the axial force T is obtained by a following equation (E3) using an integer u equal to or larger than 0 and a coefficient $a_j$ indicating a relationship between a resonant frequency ratio fr of two vibration modes of said measurement pipe and the axial force T, $$T = \sum_{j=0}^{\mu} (a_j \cdot fr^j). \tag{E3}$$

9. The vibration type measuring instrument according to claim 8, wherein
   said integer u is 2.

10. The vibration type measuring instrument according to claim 1, wherein
    said signal processing means obtains the density ρw of the fluid flowing through said measurement pipe as a convergence value of a sequence $\{\rho w_n\}$ with an initial value $\rho w_0$ given, where $\rho w_n$ of the sequence $\{\rho w_n\}$ is represented by a following equation (E4) using constants A, B, and C determined by a vibration form of said measurement pipe and a mass added to said measurement pipe, $$\rho w_n = (AEI/\omega^2 L^4 Si) + (BT(fr, \rho w_{n-1})/\omega_2 L^2 Si) + (C/LSi) \tag{E4}.$$

11. The vibration type measuring instrument according to claim 10, wherein
    a previously measured density of the fluid is applied to the initial value $\rho w_0$.

12. The vibration type measuring instrument according to claim 10, wherein
    a value $\rho w_v$ obtained by operating the sequence $\{\rho w_n\}$ v, which is an integer equal to or larger than 1, times is applied to the density ρw.

13. The vibration type measuring instrument according to claim 12, wherein
    said value v is 1.

14. The vibration type measuring instrument according to claim 10, wherein
    said signal processing means obtains the axial force T based on a ratio fr between a resonant frequency of a first vibration mode of said measurement pipe and a resonant frequency of a second vibration mode of said measurement pipe.

15. The vibration type measuring instrument according to claim 14, wherein
    said signal processing means obtains the axial force T (fr, ρw) as a function Tr expressed by a following equation (E5) using the ratio fr of resonant frequencies and a function fd (ρw) indicating an influence of the density ρw of the fluid, $$T(fr, \rho w) = Tr\{fr/fd(\rho w)\} \tag{E5}.$$

16. The vibration type measuring instrument according to claim 15, wherein
    the axial force T (fr, ρw) is obtained by a following equation (E6) using an integer p equal to or larger than 0 and a coefficient indicating a relationship between $\{fr/fd(\rho w)\}^j$ and a function Tr, $$Tr\{fr/fd(\rho w)\} = \sum_{j=0}^{p} [bj\{fr/fd(\rho w)\}^j]. \tag{E6}$$

17. The vibration type measuring instrument according to claim 16, wherein
    said integer p is 2.

18. The vibration type measuring instrument according to claim 15, wherein
    said function fd(ρw) is obtained by a following equation (E7) using an integer u equal to or larger than 0 and a coefficient aj indicating a relationship between the density ρw of the fluid and the function fd, $$fd(\rho w) = \sum_{j=0}^{\mu} (aj \cdot \rho w^j). \tag{E7}$$

19. The vibration type measuring instrument according to claim 18, wherein
    said integer u is one of 2 and 3.

20. The vibration type measuring instrument according to claim 14, wherein
    said first and second vibration modes are respectively a primary vibration mode and a tertiary vibration mode of said measurement pipe.

21. The vibration type measuring instrument according to claim 14, wherein
    said first and second vibration modes are respectively a tertiary vibration mode and a quinary vibration mode of said measurement pipe.

22. The vibration type measuring instrument according to claim 15, wherein
    said function fd (ρw) is represented as a line graph data which is obtained by linear interpolation for a plurality of frequency ratio fr data obtained for a plurality of fluid densities.

23. The vibration type measuring instrument according to claim 1, wherein the form of a function T(fr, ρw) of the axial force T is adjusted by changing the mass, the installation position for said measurement pipe, and the number of the added masses.

24. The vibration type measuring instrument according to claim 15, wherein
the form of said function fd (ρw), which is a function representing an influence of the density ρw of the fluid for the ratio fr of frequencies, is adjusted by changing the mass, the installation position for said measurement pipe, and the number of the added masses.

25. A method of measuring at least one of mass flow rate and density of a fluid flowing through a straight measurement pipe by vibrating the pipe, comprising the steps of:
detecting a vibration of a straight measurement pipe;
obtaining a resonant angular frequency ω and axial force T based on the detected vibration of the measurement pipe; and
obtaining a density ρw of the fluid flowing through the measurement pipe based on a following equation (E1) using the obtained resonant angular frequency ω and axial force T, $$\omega^2 = \left\{ EI \int_0^L (d^2y/dx^2)^2 dx - T \int_0^L y(d^2y/dx^2) dx \right\} / \left\{ (\rho w Si + \rho t St) \int_0^L y^2 dx + \sum_{k=1}^n (mk \cdot yk^2) \right\}, \quad (E1)$$

where E indicates the Young's modulus of the measurement pipe, I indicates a cross-sectional secondary moment of the measurement pipe, Si indicates a cross-sectional area of a hollow portion of the measurement pipe, ρt indicates a density of the measurement pipe, St indicates an actual cross-sectional area of the measurement pipe, L indicates a length in an axial direction of the measurement pipe, x indicates a position in the axial direction of the measurement pipe, y indicates a vibration amplitude of the measurement pipe at position x, n indicates a number of masses added to the measurement pipe, mk indicates a mass of a k-th added mass, and yk indicates a vibration amplitude of the k-th added mass.

26. The method according to claim 25, further comprising the step of:
obtaining the density ρw of the fluid flowing through the measurement pipe by a following equation (E2) obtained by solving the equation (E1) for the density ρw using constants A, B, and C determined by a vibration form of the measurement pipe and an added mass, $$\rho w (AEI/\omega^2 L^4 Si) + (BT/\omega^2 L^2 Si) + (C/LSi) \quad (E2).$$

27. The method according to claim 26, further comprising the steps of:
generating three different equations by substituting in the equation (E2) three sets of values, obtained in three different states, of the density ρw of the fluid, the Young's modulus E of said measurement pipe, the cross-sectional secondary moment I of said measurement pipe, the resonant angular frequency ω and axial force T of the measurement pipe, length L along the axial direction of the measurement pipe, and a cross-sectional area Si of the hollow portion of the measurement pipe; and
determining the constants A, B, and C by solving simultaneous equations of the three different equations.

28. The method according to claim 26, further comprising the steps of:
generating at least three different equations by substituting in the equation (E2) three sets of values, obtained in at least three different states, of the density ρw of the fluid, the Young's modulus E of said measurement pipe, the cross-sectional secondary moment I of said measurement pipe, the resonant angular frequency ω and axial force T of the measurement pipe, length L along the axial direction of said measurement pipe, and a cross-sectional area Si of the hollow portion of said measurement pipe, and
determining said constants A, B, and C by a least squares method in a way that an error among the at least three equations is minimized.

29. The method according to claim 25, further comprising the step of:
obtaining the axial force T based on a ratio between a resonant frequency of a first vibration mode of the measurement pipe and a resonant frequency of a second vibration mode of the measurement pipe.

30. The method according to claim 29, wherein
said first and second vibration modes are respectively the primary and tertiary vibration modes of the measurement pipe.

31. The method according to claim 29, wherein
said first and second vibration modes are respectively a tertiary and a quinary vibration modes of the measurement pipe.

32. The vibration type measuring instrument according to claim 29, further comprising the step of:
obtaining the axial force T by a following equation (E3) using an integer u equal to or larger than 0 and a coefficient a indicating a relationship between a resonant frequency ratio fr of two vibration modes of the measurement pipe and the axial force T, $$T = \sum_{j=0}^{\mu} (a_j \cdot f r^j), \quad (E3)$$

33. The method according to claim 32, wherein
said integer u is 2.

34. The method according to claim 25, further comprising the step of:
obtaining the density ρw of the fluid flowing through the measurement pipe as a convergence value of a sequence {ρw_n} with an initial value ρw_0 given, where ρw_n of the sequence {ρw_n} is represented by a following equation (E4) using constants A, B, and C determined by a vibration form of the measurement pipe and a mass added to the measurement pipe, $$\rho w_n = (AEI/\omega^2 L^4 Si) + (BT(fr, \rho w_{n-1})/\omega^2 L^2 Si) + (C/LSi) \quad (E4).$$

35. The method according to claim 34, further comprising the step of:
applying a previously measured density of the fluid to the initial value ρw_0.

36. The method according to claim 34, further comprising the step of:
applying a value ρw_v obtained by operating the sequence {ρw_n} v, which is an integer equal to or larger than 1, times to the density ρw.

37. The method according to claim 36, wherein said value v is 1.

38. The method according to claim 34, further comprising the step of:
   obtaining the axial force T based on a ratio fr of a resonant frequency of a first vibration mode of the measurement pipe to a resonant frequency of a second vibration mode of the measurement pipe.

39. The method according to claim 38, further comprising the step of:
   obtaining the axial force T (fr, ρw) as a function Tr expressed by a following equation (E5) using the ratio fr of resonant frequencies and a function fd (ρw) indicating an influence of the density ρw of the fluid, $$T(fr, \rho w) = Tr\{fr/fd(\rho w)\} \tag{E5}$$

40. The method according to claim 39, further comprising the step of:
   obtaining the axial force T (fr, ρw) by a following equation (E6) using an integer p equal to or larger than 0 and a coefficient indicating a relationship between $\{fr/fd(\rho w)\}^j$ and a function Tr, $$Tr\{fr/fd(\rho w)\} = \sum_{j=0}^{p}[bj\{fr/fd(\rho w)\}^j]. \tag{E6}$$

41. The method according to claim 40, wherein said integer p is 2.

42. The method according to claim 39, further comprising the step of:
   obtaining the axial force T by a following equation (E7) using an integer u equal to or larger than 0 and a coefficient aj indicating a relationship between the density ρw of the fluid and the function fd, $$fd(\rho w) = \sum_{j=0}^{\mu}(aj \cdot \rho w^j). \tag{E7}$$

43. The method according to claim 42, wherein said integer u is one of 2 and 3.

44. The method according to claim 38, wherein said first and second vibration modes are respectively a primary vibration mode and a tertiary vibration mode of said measurement pipe.

45. The method according to claim 38, wherein said first and second vibration modes are respectively a tertiary vibration mode and a quinary vibration mode of said measurement pipe.

46. The method according to claim 39, further including the step of representing said function fd (ρw) as a line graph data which is obtained by linear interpolation for a plurality of frequency ratio fr data obtained for a plurality of fluid densities.

47. The method according to claim 25, further including the step of adjusting the form of a function T(fr, ρw) of the axial force T by changing the mass, the installation position for said measurement pipe, and the number of the added masses.

48. The method according to claim 39, further including the step of adjusting the form of said function fd (ρw), which is a function representing an influence of the density ρw of the fluid for the ratio fr of frequencies, by changing the mass, the installation position for said measurement pipe, and the number of the added masses.

* * * * *